(12) United States Patent
Wang et al.

(10) Patent No.: US 12,180,499 B2
(45) Date of Patent: Dec. 31, 2024

(54) COMPOSITIONS AND METHODS FOR IMPEDING TRANSCRIPTION OF EXPANDED MICROSATELLITE REPEATS

(71) Applicant: University of Florida Research Foundation, Inc., Gainesville, FL (US)

(72) Inventors: Eric Tzy-Shi Wang, Gainesville, FL (US); Tanvi Saxena, Gainesville, FL (US); Belinda Pinto, Gainesville, FL (US); John Andrew Berglund, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1072 days.

(21) Appl. No.: 16/346,163

(22) PCT Filed: Oct. 31, 2017

(86) PCT No.: PCT/US2017/059324
§ 371 (c)(1),
(2) Date: Apr. 30, 2019

(87) PCT Pub. No.: WO2018/081806
PCT Pub. Date: May 3, 2018

(65) Prior Publication Data
US 2021/0285010 A1    Sep. 16, 2021

Related U.S. Application Data

(60) Provisional application No. 62/415,353, filed on Oct. 31, 2016.

(51) Int. Cl.
| | | |
|---|---|---|
| *C12N 15/00* | (2006.01) | |
| *A61K 31/704* | (2006.01) | |
| *A61K 38/12* | (2006.01) | |
| *A61P 21/00* | (2006.01) | |
| *C12N 9/22* | (2006.01) | |
| *C12N 15/11* | (2006.01) | |
| *C12N 15/86* | (2006.01) | |

(52) U.S. Cl.
CPC ............ *C12N 15/86* (2013.01); *A61K 31/704* (2013.01); *A61K 38/12* (2013.01); *A61P 21/00* (2018.01); *C12N 9/22* (2013.01); *C12N 15/11* (2013.01); *C12N 2310/20* (2017.05); *C12N 2750/14123* (2013.01); *C12N 2750/14143* (2013.01); *C12N 2750/14171* (2013.01); *C12N 2800/80* (2013.01)

(58) Field of Classification Search
CPC ..................... C12N 15/00; C12N 2310/20
See application file for complete search history.

(56) References Cited

U.S. PATENT DOCUMENTS

2016/0237455 A1    8/2016    Glucksmann et al.

FOREIGN PATENT DOCUMENTS

| WO | WO-2015070212 A1 * | 5/2015 | ........... A61K 31/713 |
| WO | WO-2015139139 A1 * | 9/2015 | ............. C07K 14/47 |
| WO | WO2015171932 A1 * | 11/2015 | ............. A61K 48/00 |
| WO | WO-2015173436 A1 * | 11/2015 | ............. A61K 35/34 |

OTHER PUBLICATIONS

Santiago-Ortiz et al. (2015) "AAV ancestral reconstruction library enables selection of broadly infectious viral variants" Gene therapy, 22(12), 934-946. (Year: 2015).*
Ran et al. (2015) "In vivo genome editing using *Staphylococcus aureus* Cas9" Nature 520, No. 7546: 186-191. (Year: 2015).*
International Search Report issued for PCT/US2017/059324, dated Apr. 17, 2018.
International Preliminary Report on Patentability for Application No. PCT/US2017/059324, mailed May 9, 2019.

* cited by examiner

*Primary Examiner* — Teresa E Knight
*Assistant Examiner* — James Joseph Graber
(74) *Attorney, Agent, or Firm* — Wolf, Greenfield & Sacks, P.C.

(57) ABSTRACT

Disclosed herein are compositions and methods for treating diseases characterized by expanded microsatellite repeats by impeding or inhibiting transcription of expanded microsatellite repeats.

2 Claims, 16 Drawing Sheets

Specification includes a Sequence Listing.

A Region of interest selection

All operations performed on 3D stack; maximum intensity shown here for simplicity

B Nuclei segmentation

C Background subtraction & quantitation

SEQUENCE LISTING

```
<160> NUMBER OF SEQ ID NOS: 38

<210> SEQ ID NO 1
<211> LENGTH: 18
<212> TYPE: DNA
<213> ORGANISM: Mus musculus

<400> SEQUENCE: 1
cagcagcagc agcagcag                                                   18

<210> SEQ ID NO 2
<211> LENGTH: 18
<212> TYPE: DNA
<213> ORGANISM: Mus musculus

<400> SEQUENCE: 2
ctgctgctgc tgctgctg                                                   18

<210> SEQ ID NO 3
<211> LENGTH: 18
<212> TYPE: RNA
<213> ORGANISM: Mus musculus

<400> SEQUENCE: 3
cugcugcugc ugcugcug                                                   18

<210> SEQ ID NO 4
<211> LENGTH: 18
<212> TYPE: DNA
<213> ORGANISM: Mus musculus

<400> SEQUENCE: 4
agcagcagca gcagcagc                                                   18

<210> SEQ ID NO 5
<211> LENGTH: 18
<212> TYPE: DNA
<213> ORGANISM: Mus musculus

<400> SEQUENCE: 5
gcagcagcag cagcagca                                                   18

<210> SEQ ID NO 6
<211> LENGTH: 20
<212> TYPE: PRT
<213> ORGANISM: Mus musculus

<400> SEQUENCE: 6

Cys Ala Gly Gly Cys Ala Gly Gly Cys Ala Gly Gly Cys Ala Gly Gly
1               5                   10                  15

Cys Ala Gly Gly
            20

<210> SEQ ID NO 7
<211> LENGTH: 20
<212> TYPE: DNA
```

<213> ORGANISM: Mus musculus

<400> SEQUENCE: 7
aggcaggcag gcaggcaggc                                          20

<210> SEQ ID NO 8
<211> LENGTH: 20
<212> TYPE: DNA
<213> ORGANISM: Mus musculus

<400> SEQUENCE: 8
ggcaggcagg caggcaggca                                          20

<210> SEQ ID NO 9
<211> LENGTH: 20
<212> TYPE: DNA
<213> ORGANISM: Mus musculus

<400> SEQUENCE: 9
gcaggcaggc aggcaggcag                                          20

<210> SEQ ID NO 10
<211> LENGTH: 18
<212> TYPE: DNA
<213> ORGANISM: Mus musculus

<400> SEQUENCE: 10
ccccggcccc ggccccgg                                            18

<210> SEQ ID NO 11
<211> LENGTH: 18
<212> TYPE: DNA
<213> ORGANISM: Mus musculus

<400> SEQUENCE: 11
ggggccgggg ccggggcc                                            18

<210> SEQ ID NO 12
<211> LENGTH: 24
<212> TYPE: DNA
<213> ORGANISM: Mus musculus

<400> SEQUENCE: 12
caggcaggca ggcaggcagg cagg                                     24

<210> SEQ ID NO 13
<211> LENGTH: 24
<212> TYPE: DNA
<213> ORGANISM: Mus musculus

<400> SEQUENCE: 13
cctgcctgcc tgcctgcctg cctg                                     24

<210> SEQ ID NO 14
<211> LENGTH: 960
<212> TYPE: DNA
<213> ORGANISM: Mus musculus

<400> SEQUENCE: 14
cctgcctgcc tgcctgcctg cctgcctgcc tgcctgcctg cctgcctgcc tgcctgcctg    60
cctgcctgcc tgcctgcctg cctgcctgcc tgcctgcctg cctgcctgcc tgcctgcctg   120
cctgcctgcc tgcctgcctg cctgcctgcc tgcctgcctg cctgcctgcc tgcctgcctg   180

| | |
|---|---|
| cctgcctgcc tgcctgcctg cctgcctgcc tgcctgcctg cctgcctgcc tgcctgcctg | 240 |
| cctgcctgcc tgcctgcctg cctgcctgcc tgcctgcctg cctgcctgcc tgcctgcctg | 300 |
| cctgcctgcc tgcctgcctg cctgcctgcc tgcctgcctg cctgcctgcc tgcctgcctg | 360 |
| cctgcctgcc tgcctgcctg cctgcctgcc tgcctgcctg cctgcctgcc tgcctgcctg | 420 |
| cctgcctgcc tgcctgcctg cctgcctgcc tgcctgcctg cctgcctgcc tgcctgcctg | 480 |
| cctgcctgcc tgcctgcctg cctgcctgcc tgcctgcctg cctgcctgcc tgcctgcctg | 540 |
| cctgcctgcc tgcctgcctg cctgcctgcc tgcctgcctg cctgcctgcc tgcctgcctg | 600 |
| cctgcctgcc tgcctgcctg cctgcctgcc tgcctgcctg cctgcctgcc tgcctgcctg | 660 |
| cctgcctgcc tgcctgcctg cctgcctgcc tgcctgcctg cctgcctgcc tgcctgcctg | 720 |
| cctgcctgcc tgcctgcctg cctgcctgcc tgcctgcctg cctgcctgcc tgcctgcctg | 780 |
| cctgcctgcc tgcctgcctg cctgcctgcc tgcctgcctg cctgcctgcc tgcctgcctg | 840 |
| cctgcctgcc tgcctgcctg cctgcctgcc tgcctgcctg cctgcctgcc tgcctgcctg | 900 |
| cctgcctgcc tgcctgcctg cctgcctgcc tgcctgcctg cctgcctgcc tgcctgcctg | 960 |

```
<210> SEQ ID NO 15
<211> LENGTH: 20
<212> TYPE: RNA
<213> ORGANISM: Mus musculus

<400> SEQUENCE: 15
```

| | |
|---|---|
| ccugccugcc ugccugccug | 20 |

```
<210> SEQ ID NO 16
<211> LENGTH: 1440
<212> TYPE: DNA
<213> ORGANISM: Mus musculus

<400> SEQUENCE: 16
```

| | |
|---|---|
| ctgctgctgc tgctgctgct gctgctgctg ctgctgctgc tgctgctgct gctgctgctg | 60 |
| ctgctgctgc tgctgctgct gctgctgctg ctgctgctgc tgctgctgct gctgctgctg | 120 |
| ctgctgctgc tgctgctgct gctgctgctg ctgctgctgc tgctgctgct gctgctgctg | 180 |
| ctgctgctgc tgctgctgct gctgctgctg ctgctgctgc tgctgctgct gctgctgctg | 240 |
| ctgctgctgc tgctgctgct gctgctgctg ctgctgctgc tgctgctgct gctgctgctg | 300 |
| ctgctgctgc tgctgctgct gctgctgctg ctgctgctgc tgctgctgct gctgctgctg | 360 |
| ctgctgctgc tgctgctgct gctgctgctg ctgctgctgc tgctgctgct gctgctgctg | 420 |
| ctgctgctgc tgctgctgct gctgctgctg ctgctgctgc tgctgctgct gctgctgctg | 480 |
| ctgctgctgc tgctgctgct gctgctgctg ctgctgctgc tgctgctgct gctgctgctg | 540 |
| ctgctgctgc tgctgctgct gctgctgctg ctgctgctgc tgctgctgct gctgctgctg | 600 |
| ctgctgctgc tgctgctgct gctgctgctg ctgctgctgc tgctgctgct gctgctgctg | 660 |
| ctgctgctgc tgctgctgct gctgctgctg ctgctgctgc tgctgctgct gctgctgctg | 720 |
| ctgctgctgc tgctgctgct gctgctgctg ctgctgctgc tgctgctgct gctgctgctg | 780 |
| ctgctgctgc tgctgctgct gctgctgctg ctgctgctgc tgctgctgct gctgctgctg | 840 |
| ctgctgctgc tgctgctgct gctgctgctg ctgctgctgc tgctgctgct gctgctgctg | 900 |
| ctgctgctgc tgctgctgct gctgctgctg ctgctgctgc tgctgctgct gctgctgctg | 960 |
| ctgctgctgc tgctgctgct gctgctgctg ctgctgctgc tgctgctgct gctgctgctg | 1020 |

```
ctgctgctgc tgctgctgct gctgctgctg ctgctgctgc tgctgctgct gctgctgctg    1080
ctgctgctgc tgctgctgct gctgctgctg ctgctgctgc tgctgctgct gctgctgctg    1140
ctgctgctgc tgctgctgct gctgctgctg ctgctgctgc tgctgctgct gctgctgctg    1200
ctgctgctgc tgctgctgct gctgctgctg ctgctgctgc tgctgctgct gctgctgctg    1260
ctgctgctgc tgctgctgct gctgctgctg ctgctgctgc tgctgctgct gctgctgctg    1320
ctgctgctgc tgctgctgct gctgctgctg ctgctgctgc tgctgctgct gctgctgctg    1380
ctgctgctgc tgctgctgct gctgctgctg ctgctgctgc tgctgctgct gctgctgctg    1440

<210> SEQ ID NO 17
<211> LENGTH: 315
<212> TYPE: DNA
<213> ORGANISM: Mus musculus

<400> SEQUENCE: 17
ctgctgctgc tgctgctgct gctgctgctg ctgctgctgc tgctgctgct gctgctgctg      60
ctgctgctgc tgctgctgct gctgctgctg ctgctgctgc tgctgctgct gctgctgctg     120
ctgctgctgc tgctgctgct gctgctgctg ctgctgctgc tgctgctgct gctgctgctg     180
ctgctgctgc tgctgctgct gctgctgctg ctgctgctgc tgctgctgct gctgctgctg     240
ctgctgctgc tgctgctgct gctgctgctg ctgctgctgc tgctgctgct gctgctgctg     300
ctgctgctgc tgctg                                                      315

<210> SEQ ID NO 18
<211> LENGTH: 548
<212> TYPE: DNA
<213> ORGANISM: Mus musculus

<400> SEQUENCE: 18
cctgcctgcc tgcctgcctg cctgcctgcc tgcctgcctg cctgcctgcc tgcctgcctg      60
cctgcctgcc tgcctgcctg cctgcctgcc tgcctgcctg cctgcctgcc tgcctgcctg     120
cctgcctgcc tgcctgcctg cctgcctgcc tgcctgcctg cctgcctgcc tgcctgcctg     180
cctgcctgcc tgcctgcctg cctgcctgcc tgcctgcctg cctgcctgcc tgcctgcctg     240
cctgcctgcc tgcctgcctg cctgcctgcc tgcctgcctg cctgcctgcc tgcctgcctg     300
cctgcctgcc tgcctgcctg cctgcctgcc tgcctgcctg cctgcctgcc tgcctgcctg     360
cctgcctgcc tgcctgcctg cctgcctgcc tgcctgcctg cctgcctgcc tgcctgcctg     420
cctgcctgcc tgcctgcctg cctgcctgcc tgcctgcctg cctgcctgcc tgcctgcctg     480
cctgcctgcc tgcctgcctg cctgcctgcc tgcctgcctg cctgcctgcc tgcctgcctg     540
cctgcctg                                                              548

<210> SEQ ID NO 19
<211> LENGTH: 960
<212> TYPE: RNA
<213> ORGANISM: Mus musculus

<400> SEQUENCE: 19
ccugccugcc ugccugccug ccugccugcc ugccugccug ccugccugcc ugccugccug      60
ccugccugcc ugccugccug ccugccugcc ugccugccug ccugccugcc ugccugccug     120
ccugccugcc ugccugccug ccugccugcc ugccugccug ccugccugcc ugccugccug     180
ccugccugcc ugccugccug ccugccugcc ugccugccug ccugccugcc ugccugccug     240
ccugccugcc ugccugccug ccugccugcc ugccugccug ccugccugcc ugccugccug     300
```

-continued

| | |
|---|---|
| ccugccugcc ugccugccug ccugccugcc ugccugccug ccugccugcc ugccugccug | 360 |
| ccugccugcc ugccugccug ccugccugcc ugccugccug ccugccugcc ugccugccug | 420 |
| ccugccugcc ugccugccug ccugccugcc ugccugccug ccugccugcc ugccugccug | 480 |
| ccugccugcc ugccugccug ccugccugcc ugccugccug ccugccugcc ugccugccug | 540 |
| ccugccugcc ugccugccug ccugccugcc ugccugccug ccugccugcc ugccugccug | 600 |
| ccugccugcc ugccugccug ccugccugcc ugccugccug ccugccugcc ugccugccug | 660 |
| ccugccugcc ugccugccug ccugccugcc ugccugccug ccugccugcc ugccugccug | 720 |
| ccugccugcc ugccugccug ccugccugcc ugccugccug ccugccugcc ugccugccug | 780 |
| ccugccugcc ugccugccug ccugccugcc ugccugccug ccugccugcc ugccugccug | 840 |
| ccugccugcc ugccugccug ccugccugcc ugccugccug ccugccugcc ugccugccug | 900 |
| ccugccugcc ugccugccug ccugccugcc ugccugccug ccugccugcc ugccugccug | 960 |

<210> SEQ ID NO 20
<211> LENGTH: 720
<212> TYPE: DNA
<213> ORGANISM: Mus musculus

<400> SEQUENCE: 20

| | |
|---|---|
| ggggccgggg ccggggccgg ggccggggcc ggggccgggg ccggggccgg ggccggggcc | 60 |
| ggggccgggg ccggggccgg ggccggggcc ggggccgggg ccggggccgg ggccggggcc | 120 |
| ggggccgggg ccggggccgg ggccggggcc ggggccgggg ccggggccgg ggccggggcc | 180 |
| ggggccgggg ccggggccgg ggccggggcc ggggccgggg ccggggccgg ggccggggcc | 240 |
| ggggccgggg ccggggccgg ggccggggcc ggggccgggg ccggggccgg ggccggggcc | 300 |
| ggggccgggg ccggggccgg ggccggggcc ggggccgggg ccggggccgg ggccggggcc | 360 |
| ggggccgggg ccggggccgg ggccggggcc ggggccgggg ccggggccgg ggccggggcc | 420 |
| ggggccgggg ccggggccgg ggccggggcc ggggccgggg ccggggccgg ggccggggcc | 480 |
| ggggccgggg ccggggccgg ggccggggcc ggggccgggg ccggggccgg ggccggggcc | 540 |
| ggggccgggg ccggggccgg ggccggggcc ggggccgggg ccggggccgg ggccggggcc | 600 |
| ggggccgggg ccggggccgg ggccggggcc ggggccgggg ccggggccgg ggccggggcc | 660 |
| ggggccgggg ccggggccgg ggccggggcc ggggccgggg ccggggccgg ggccggggcc | 720 |

<210> SEQ ID NO 21
<211> LENGTH: 2880
<212> TYPE: DNA
<213> ORGANISM: Mus musculus

<400> SEQUENCE: 21

| | |
|---|---|
| cagcagcagc agcagcagca gcagcagcag cagcagcagc agcagcagca gcagcagcag | 60 |
| cagcagcagc agcagcagca gcagcagcag cagcagcagc agcagcagca gcagcagcag | 120 |
| cagcagcagc agcagcagca gcagcagcag cagcagcagc agcagcagca gcagcagcag | 180 |
| cagcagcagc agcagcagca gcagcagcag cagcagcagc agcagcagca gcagcagcag | 240 |
| cagcagcagc agcagcagca gcagcagcag cagcagcagc agcagcagca gcagcagcag | 300 |
| cagcagcagc agcagcagca gcagcagcag cagcagcagc agcagcagca gcagcagcag | 360 |
| cagcagcagc agcagcagca gcagcagcag cagcagcagc agcagcagca gcagcagcag | 420 |
| cagcagcagc agcagcagca gcagcagcag cagcagcagc agcagcagca gcagcagcag | 480 |

```
cagcagcagc agcagcagca gcagcagcag cagcagcagc agcagcagca gcagcagcag    540
cagcagcagc agcagcagca gcagcagcag cagcagcagc agcagcagca gcagcagcag    600
cagcagcagc agcagcagca gcagcagcag cagcagcagc agcagcagca gcagcagcag    660
cagcagcagc agcagcagca gcagcagcag cagcagcagc agcagcagca gcagcagcag    720
cagcagcagc agcagcagca gcagcagcag cagcagcagc agcagcagca gcagcagcag    780
cagcagcagc agcagcagca gcagcagcag cagcagcagc agcagcagca gcagcagcag    840
cagcagcagc agcagcagca gcagcagcag cagcagcagc agcagcagca gcagcagcag    900
cagcagcagc agcagcagca gcagcagcag cagcagcagc agcagcagca gcagcagcag    960
cagcagcagc agcagcagca gcagcagcag cagcagcagc agcagcagca gcagcagcag   1020
cagcagcagc agcagcagca gcagcagcag cagcagcagc agcagcagca gcagcagcag   1080
cagcagcagc agcagcagca gcagcagcag cagcagcagc agcagcagca gcagcagcag   1140
cagcagcagc agcagcagca gcagcagcag cagcagcagc agcagcagca gcagcagcag   1200
cagcagcagc agcagcagca gcagcagcag cagcagcagc agcagcagca gcagcagcag   1260
cagcagcagc agcagcagca gcagcagcag cagcagcagc agcagcagca gcagcagcag   1320
cagcagcagc agcagcagca gcagcagcag cagcagcagc agcagcagca gcagcagcag   1380
cagcagcagc agcagcagca gcagcagcag cagcagcagc agcagcagca gcagcagcag   1440
cagcagcagc agcagcagca gcagcagcag cagcagcagc agcagcagca gcagcagcag   1500
cagcagcagc agcagcagca gcagcagcag cagcagcagc agcagcagca gcagcagcag   1560
cagcagcagc agcagcagca gcagcagcag cagcagcagc agcagcagca gcagcagcag   1620
cagcagcagc agcagcagca gcagcagcag cagcagcagc agcagcagca gcagcagcag   1680
cagcagcagc agcagcagca gcagcagcag cagcagcagc agcagcagca gcagcagcag   1740
cagcagcagc agcagcagca gcagcagcag cagcagcagc agcagcagca gcagcagcag   1800
cagcagcagc agcagcagca gcagcagcag cagcagcagc agcagcagca gcagcagcag   1860
cagcagcagc agcagcagca gcagcagcag cagcagcagc agcagcagca gcagcagcag   1920
cagcagcagc agcagcagca gcagcagcag cagcagcagc agcagcagca gcagcagcag   1980
cagcagcagc agcagcagca gcagcagcag cagcagcagc agcagcagca gcagcagcag   2040
cagcagcagc agcagcagca gcagcagcag cagcagcagc agcagcagca gcagcagcag   2100
cagcagcagc agcagcagca gcagcagcag cagcagcagc agcagcagca gcagcagcag   2160
cagcagcagc agcagcagca gcagcagcag cagcagcagc agcagcagca gcagcagcag   2220
cagcagcagc agcagcagca gcagcagcag cagcagcagc agcagcagca gcagcagcag   2280
cagcagcagc agcagcagca gcagcagcag cagcagcagc agcagcagca gcagcagcag   2340
cagcagcagc agcagcagca gcagcagcag cagcagcagc agcagcagca gcagcagcag   2400
cagcagcagc agcagcagca gcagcagcag cagcagcagc agcagcagca gcagcagcag   2460
cagcagcagc agcagcagca gcagcagcag cagcagcagc agcagcagca gcagcagcag   2520
cagcagcagc agcagcagca gcagcagcag cagcagcagc agcagcagca gcagcagcag   2580
cagcagcagc agcagcagca gcagcagcag cagcagcagc agcagcagca gcagcagcag   2640
cagcagcagc agcagcagca gcagcagcag cagcagcagc agcagcagca gcagcagcag   2700
cagcagcagc agcagcagca gcagcagcag cagcagcagc agcagcagca gcagcagcag   2760
cagcagcagc agcagcagca gcagcagcag cagcagcagc agcagcagca gcagcagcag   2820
cagcagcagc agcagcagca gcagcagcag cagcagcagc agcagcagca gcagcagcag   2880
```

<210> SEQ ID NO 22
<211> LENGTH: 960
<212> TYPE: DNA
<213> ORGANISM: Mus musculus

<400> SEQUENCE: 22

| | | | | | |
|---|---|---|---|---|---|
| caggcaggca | ggcaggcagg | caggcaggca | ggcaggcagg | caggcaggca | ggcaggcagg | 60 |
| caggcaggca | ggcaggcagg | caggcaggca | ggcaggcagg | caggcaggca | ggcaggcagg | 120 |
| caggcaggca | ggcaggcagg | caggcaggca | ggcaggcagg | caggcaggca | ggcaggcagg | 180 |
| caggcaggca | ggcaggcagg | caggcaggca | ggcaggcagg | caggcaggca | ggcaggcagg | 240 |
| caggcaggca | ggcaggcagg | caggcaggca | ggcaggcagg | caggcaggca | ggcaggcagg | 300 |
| caggcaggca | ggcaggcagg | caggcaggca | ggcaggcagg | caggcaggca | ggcaggcagg | 360 |
| caggcaggca | ggcaggcagg | caggcaggca | ggcaggcagg | caggcaggca | ggcaggcagg | 420 |
| caggcaggca | ggcaggcagg | caggcaggca | ggcaggcagg | caggcaggca | ggcaggcagg | 480 |
| caggcaggca | ggcaggcagg | caggcaggca | ggcaggcagg | caggcaggca | ggcaggcagg | 540 |
| caggcaggca | ggcaggcagg | caggcaggca | ggcaggcagg | caggcaggca | ggcaggcagg | 600 |
| caggcaggca | ggcaggcagg | caggcaggca | ggcaggcagg | caggcaggca | ggcaggcagg | 660 |
| caggcaggca | ggcaggcagg | caggcaggca | ggcaggcagg | caggcaggca | ggcaggcagg | 720 |
| caggcaggca | ggcaggcagg | caggcaggca | ggcaggcagg | caggcaggca | ggcaggcagg | 780 |
| caggcaggca | ggcaggcagg | caggcaggca | ggcaggcagg | caggcaggca | ggcaggcagg | 840 |
| caggcaggca | ggcaggcagg | caggcaggca | ggcaggcagg | caggcaggca | ggcaggcagg | 900 |
| caggcaggca | ggcaggcagg | caggcaggca | ggcaggcagg | caggcaggca | ggcaggcagg | 960 |

<210> SEQ ID NO 23
<211> LENGTH: 2880
<212> TYPE: DNA
<213> ORGANISM: Mus musculus

<400> SEQUENCE: 23

| | | | | | |
|---|---|---|---|---|---|
| ctgctgctgc | tgctgctgct | gctgctgctg | ctgctgctgc | tgctgctgct | gctgctgctg | 60 |
| ctgctgctgc | tgctgctgct | gctgctgctg | ctgctgctgc | tgctgctgct | gctgctgctg | 120 |
| ctgctgctgc | tgctgctgct | gctgctgctg | ctgctgctgc | tgctgctgct | gctgctgctg | 180 |
| ctgctgctgc | tgctgctgct | gctgctgctg | ctgctgctgc | tgctgctgct | gctgctgctg | 240 |
| ctgctgctgc | tgctgctgct | gctgctgctg | ctgctgctgc | tgctgctgct | gctgctgctg | 300 |
| ctgctgctgc | tgctgctgct | gctgctgctg | ctgctgctgc | tgctgctgct | gctgctgctg | 360 |
| ctgctgctgc | tgctgctgct | gctgctgctg | ctgctgctgc | tgctgctgct | gctgctgctg | 420 |
| ctgctgctgc | tgctgctgct | gctgctgctg | ctgctgctgc | tgctgctgct | gctgctgctg | 480 |
| ctgctgctgc | tgctgctgct | gctgctgctg | ctgctgctgc | tgctgctgct | gctgctgctg | 540 |
| ctgctgctgc | tgctgctgct | gctgctgctg | ctgctgctgc | tgctgctgct | gctgctgctg | 600 |
| ctgctgctgc | tgctgctgct | gctgctgctg | ctgctgctgc | tgctgctgct | gctgctgctg | 660 |
| ctgctgctgc | tgctgctgct | gctgctgctg | ctgctgctgc | tgctgctgct | gctgctgctg | 720 |
| ctgctgctgc | tgctgctgct | gctgctgctg | ctgctgctgc | tgctgctgct | gctgctgctg | 780 |
| ctgctgctgc | tgctgctgct | gctgctgctg | ctgctgctgc | tgctgctgct | gctgctgctg | 840 |
| ctgctgctgc | tgctgctgct | gctgctgctg | ctgctgctgc | tgctgctgct | gctgctgctg | 900 |

| | | |
|---|---|---|
| ctgctgctgc tgctgctgct gctgctgctg ctgctgctgc tgctgctgct gctgctgctg | 960 | |
| ctgctgctgc tgctgctgct gctgctgctg ctgctgctgc tgctgctgct gctgctgctg | 1020 | |
| ctgctgctgc tgctgctgct gctgctgctg ctgctgctgc tgctgctgct gctgctgctg | 1080 | |
| ctgctgctgc tgctgctgct gctgctgctg ctgctgctgc tgctgctgct gctgctgctg | 1140 | |
| ctgctgctgc tgctgctgct gctgctgctg ctgctgctgc tgctgctgct gctgctgctg | 1200 | |
| ctgctgctgc tgctgctgct gctgctgctg ctgctgctgc tgctgctgct gctgctgctg | 1260 | |
| ctgctgctgc tgctgctgct gctgctgctg ctgctgctgc tgctgctgct gctgctgctg | 1320 | |
| ctgctgctgc tgctgctgct gctgctgctg ctgctgctgc tgctgctgct gctgctgctg | 1380 | |
| ctgctgctgc tgctgctgct gctgctgctg ctgctgctgc tgctgctgct gctgctgctg | 1440 | |
| ctgctgctgc tgctgctgct gctgctgctg ctgctgctgc tgctgctgct gctgctgctg | 1500 | |
| ctgctgctgc tgctgctgct gctgctgctg ctgctgctgc tgctgctgct gctgctgctg | 1560 | |
| ctgctgctgc tgctgctgct gctgctgctg ctgctgctgc tgctgctgct gctgctgctg | 1620 | |
| ctgctgctgc tgctgctgct gctgctgctg ctgctgctgc tgctgctgct gctgctgctg | 1680 | |
| ctgctgctgc tgctgctgct gctgctgctg ctgctgctgc tgctgctgct gctgctgctg | 1740 | |
| ctgctgctgc tgctgctgct gctgctgctg ctgctgctgc tgctgctgct gctgctgctg | 1800 | |
| ctgctgctgc tgctgctgct gctgctgctg ctgctgctgc tgctgctgct gctgctgctg | 1860 | |
| ctgctgctgc tgctgctgct gctgctgctg ctgctgctgc tgctgctgct gctgctgctg | 1920 | |
| ctgctgctgc tgctgctgct gctgctgctg ctgctgctgc tgctgctgct gctgctgctg | 1980 | |
| ctgctgctgc tgctgctgct gctgctgctg ctgctgctgc tgctgctgct gctgctgctg | 2040 | |
| ctgctgctgc tgctgctgct gctgctgctg ctgctgctgc tgctgctgct gctgctgctg | 2100 | |
| ctgctgctgc tgctgctgct gctgctgctg ctgctgctgc tgctgctgct gctgctgctg | 2160 | |
| ctgctgctgc tgctgctgct gctgctgctg ctgctgctgc tgctgctgct gctgctgctg | 2220 | |
| ctgctgctgc tgctgctgct gctgctgctg ctgctgctgc tgctgctgct gctgctgctg | 2280 | |
| ctgctgctgc tgctgctgct gctgctgctg ctgctgctgc tgctgctgct gctgctgctg | 2340 | |
| ctgctgctgc tgctgctgct gctgctgctg ctgctgctgc tgctgctgct gctgctgctg | 2400 | |
| ctgctgctgc tgctgctgct gctgctgctg ctgctgctgc tgctgctgct gctgctgctg | 2460 | |
| ctgctgctgc tgctgctgct gctgctgctg ctgctgctgc tgctgctgct gctgctgctg | 2520 | |
| ctgctgctgc tgctgctgct gctgctgctg ctgctgctgc tgctgctgct gctgctgctg | 2580 | |
| ctgctgctgc tgctgctgct gctgctgctg ctgctgctgc tgctgctgct gctgctgctg | 2640 | |
| ctgctgctgc tgctgctgct gctgctgctg ctgctgctgc tgctgctgct gctgctgctg | 2700 | |
| ctgctgctgc tgctgctgct gctgctgctg ctgctgctgc tgctgctgct gctgctgctg | 2760 | |
| ctgctgctgc tgctgctgct gctgctgctg ctgctgctgc tgctgctgct gctgctgctg | 2820 | |
| ctgctgctgc tgctgctgct gctgctgctg ctgctgctgc tgctgctgct gctgctgctg | 2880 | |

<210> SEQ ID NO 24
<211> LENGTH: 2880
<212> TYPE: RNA
<213> ORGANISM: Mus musculus

<400> SEQUENCE: 24

| | | |
|---|---|---|
| cugcugcugc ugcugcugcu gcugcugcug cugcugcugc ugcugcugcu gcugcugcug | 60 | |
| cugcugcugc ugcugcugcu gcugcugcug cugcugcugc ugcugcugcu gcugcugcug | 120 | |
| cugcugcugc ugcugcugcu gcugcugcug cugcugcugc ugcugcugcu gcugcugcug | 180 | |

-continued cugcugcugc ugcugcugcu gcugcugcug cugcugcugc ugcugcugcu gcugcugcug 240
cugcugcugc ugcugcugcu gcugcugcug cugcugcugc ugcugcugcu gcugcugcug 300
cugcugcugc ugcugcugcu gcugcugcug cugcugcugc ugcugcugcu gcugcugcug 360
cugcugcugc ugcugcugcu gcugcugcug cugcugcugc ugcugcugcu gcugcugcug 420
cugcugcugc ugcugcugcu gcugcugcug cugcugcugc ugcugcugcu gcugcugcug 480
cugcugcugc ugcugcugcu gcugcugcug cugcugcugc ugcugcugcu gcugcugcug 540
cugcugcugc ugcugcugcu gcugcugcug cugcugcugc ugcugcugcu gcugcugcug 600
cugcugcugc ugcugcugcu gcugcugcug cugcugcugc ugcugcugcu gcugcugcug 660
cugcugcugc ugcugcugcu gcugcugcug cugcugcugc ugcugcugcu gcugcugcug 720
cugcugcugc ugcugcugcu gcugcugcug cugcugcugc ugcugcugcu gcugcugcug 780
cugcugcugc ugcugcugcu gcugcugcug cugcugcugc ugcugcugcu gcugcugcug 840
cugcugcugc ugcugcugcu gcugcugcug cugcugcugc ugcugcugcu gcugcugcug 900
cugcugcugc ugcugcugcu gcugcugcug cugcugcugc ugcugcugcu gcugcugcug 960
cugcugcugc ugcugcugcu gcugcugcug cugcugcugc ugcugcugcu gcugcugcug 1020
cugcugcugc ugcugcugcu gcugcugcug cugcugcugc ugcugcugcu gcugcugcug 1080
cugcugcugc ugcugcugcu gcugcugcug cugcugcugc ugcugcugcu gcugcugcug 1140
cugcugcugc ugcugcugcu gcugcugcug cugcugcugc ugcugcugcu gcugcugcug 1200
cugcugcugc ugcugcugcu gcugcugcug cugcugcugc ugcugcugcu gcugcugcug 1260
cugcugcugc ugcugcugcu gcugcugcug cugcugcugc ugcugcugcu gcugcugcug 1320
cugcugcugc ugcugcugcu gcugcugcug cugcugcugc ugcugcugcu gcugcugcug 1380
cugcugcugc ugcugcugcu gcugcugcug cugcugcugc ugcugcugcu gcugcugcug 1440
cugcugcugc ugcugcugcu gcugcugcug cugcugcugc ugcugcugcu gcugcugcug 1500
cugcugcugc ugcugcugcu gcugcugcug cugcugcugc ugcugcugcu gcugcugcug 1560
cugcugcugc ugcugcugcu gcugcugcug cugcugcugc ugcugcugcu gcugcugcug 1620
cugcugcugc ugcugcugcu gcugcugcug cugcugcugc ugcugcugcu gcugcugcug 1680
cugcugcugc ugcugcugcu gcugcugcug cugcugcugc ugcugcugcu gcugcugcug 1740
cugcugcugc ugcugcugcu gcugcugcug cugcugcugc ugcugcugcu gcugcugcug 1800
cugcugcugc ugcugcugcu gcugcugcug cugcugcugc ugcugcugcu gcugcugcug 1860
cugcugcugc ugcugcugcu gcugcugcug cugcugcugc ugcugcugcu gcugcugcug 1920
cugcugcugc ugcugcugcu gcugcugcug cugcugcugc ugcugcugcu gcugcugcug 1980
cugcugcugc ugcugcugcu gcugcugcug cugcugcugc ugcugcugcu gcugcugcug 2040
cugcugcugc ugcugcugcu gcugcugcug cugcugcugc ugcugcugcu gcugcugcug 2100
cugcugcugc ugcugcugcu gcugcugcug cugcugcugc ugcugcugcu gcugcugcug 2160
cugcugcugc ugcugcugcu gcugcugcug cugcugcugc ugcugcugcu gcugcugcug 2220
cugcugcugc ugcugcugcu gcugcugcug cugcugcugc ugcugcugcu gcugcugcug 2280
cugcugcugc ugcugcugcu gcugcugcug cugcugcugc ugcugcugcu gcugcugcug 2340
cugcugcugc ugcugcugcu gcugcugcug cugcugcugc ugcugcugcu gcugcugcug 2400
cugcugcugc ugcugcugcu gcugcugcug cugcugcugc ugcugcugcu gcugcugcug 2460
cugcugcugc ugcugcugcu gcugcugcug cugcugcugc ugcugcugcu gcugcugcug 2520

| | |
|---|---|
| cugcugcugc ugcugcugcu gcugcugcug cugcugcugc ugcugcugcu gcugcugcug | 2580 |
| cugcugcugc ugcugcugcu gcugcugcug cugcugcugc ugcugcugcu gcugcugcug | 2640 |
| cugcugcugc ugcugcugcu gcugcugcug cugcugcugc ugcugcugcu gcugcugcug | 2700 |
| cugcugcugc ugcugcugcu gcugcugcug cugcugcugc ugcugcugcu gcugcugcug | 2760 |
| cugcugcugc ugcugcugcu gcugcugcug cugcugcugc ugcugcugcu gcugcugcug | 2820 |
| cugcugcugc ugcugcugcu gcugcugcug cugcugcugc ugcugcugcu gcugcugcug | 2880 |

<210> SEQ ID NO 25
<211> LENGTH: 20
<212> TYPE: DNA
<213> ORGANISM: Mus musculus

<400> SEQUENCE: 25

| | |
|---|---|
| cctgcctgcc tgcctgcctg | 20 |

<210> SEQ ID NO 26
<211> LENGTH: 1440
<212> TYPE: RNA
<213> ORGANISM: Mus musculus

<400> SEQUENCE: 26

| | |
|---|---|
| cugcugcugc ugcugcugcu gcugcugcug cugcugcugc ugcugcugcu gcugcugcug | 60 |
| cugcugcugc ugcugcugcu gcugcugcug cugcugcugc ugcugcugcu gcugcugcug | 120 |
| cugcugcugc ugcugcugcu gcugcugcug cugcugcugc ugcugcugcu gcugcugcug | 180 |
| cugcugcugc ugcugcugcu gcugcugcug cugcugcugc ugcugcugcu gcugcugcug | 240 |
| cugcugcugc ugcugcugcu gcugcugcug cugcugcugc ugcugcugcu gcugcugcug | 300 |
| cugcugcugc ugcugcugcu gcugcugcug cugcugcugc ugcugcugcu gcugcugcug | 360 |
| cugcugcugc ugcugcugcu gcugcugcug cugcugcugc ugcugcugcu gcugcugcug | 420 |
| cugcugcugc ugcugcugcu gcugcugcug cugcugcugc ugcugcugcu gcugcugcug | 480 |
| cugcugcugc ugcugcugcu gcugcugcug cugcugcugc ugcugcugcu gcugcugcug | 540 |
| cugcugcugc ugcugcugcu gcugcugcug cugcugcugc ugcugcugcu gcugcugcug | 600 |
| cugcugcugc ugcugcugcu gcugcugcug cugcugcugc ugcugcugcu gcugcugcug | 660 |
| cugcugcugc ugcugcugcu gcugcugcug cugcugcugc ugcugcugcu gcugcugcug | 720 |
| cugcugcugc ugcugcugcu gcugcugcug cugcugcugc ugcugcugcu gcugcugcug | 780 |
| cugcugcugc ugcugcugcu gcugcugcug cugcugcugc ugcugcugcu gcugcugcug | 840 |
| cugcugcugc ugcugcugcu gcugcugcug cugcugcugc ugcugcugcu gcugcugcug | 900 |
| cugcugcugc ugcugcugcu gcugcugcug cugcugcugc ugcugcugcu gcugcugcug | 960 |
| cugcugcugc ugcugcugcu gcugcugcug cugcugcugc ugcugcugcu gcugcugcug | 1020 |
| cugcugcugc ugcugcugcu gcugcugcug cugcugcugc ugcugcugcu gcugcugcug | 1080 |
| cugcugcugc ugcugcugcu gcugcugcug cugcugcugc ugcugcugcu gcugcugcug | 1140 |
| cugcugcugc ugcugcugcu gcugcugcug cugcugcugc ugcugcugcu gcugcugcug | 1200 |
| cugcugcugc ugcugcugcu gcugcugcug cugcugcugc ugcugcugcu gcugcugcug | 1260 |
| cugcugcugc ugcugcugcu gcugcugcug cugcugcugc ugcugcugcu gcugcugcug | 1320 |
| cugcugcugc ugcugcugcu gcugcugcug cugcugcugc ugcugcugcu gcugcugcug | 1380 |
| cugcugcugc ugcugcugcu gcugcugcug cugcugcugc ugcugcugcu gcugcugcug | 1440 |

```
<210> SEQ ID NO 27
<211> LENGTH: 85
<212> TYPE: DNA
<213> ORGANISM: Mus musculus

<400> SEQUENCE: 27
tcgacctgcc tgcctgcctg cctgcctgcc tgcctgcctg cctgcctgcc tgcctgcctg    60
cctgcctgcc tgcctgcctg cctgc                                         85

<210> SEQ ID NO 28
<211> LENGTH: 65
<212> TYPE: DNA
<213> ORGANISM: Mus musculus

<400> SEQUENCE: 28
tcgagcagca gcagcagcag cagcagcagc agcagcagca gcagcagcag cagcagcagc    60
agcag                                                               65

<210> SEQ ID NO 29
<211> LENGTH: 450
<212> TYPE: DNA
<213> ORGANISM: Mus musculus

<400> SEQUENCE: 29
ctgctgctgc tgctgctgct gctgctgctg ctgctgctgc tgctgctgct gctgctgctg    60
ctgctgctgc tgctgctgct gctgctgctg ctgctgctgc tgctgctgct gctgctgctg   120
ctgctgctgc tgctgctgct gctgctgctg ctgctgctgc tgctgctgct gctgctgctg   180
ctgctgctgc tgctgctgct gctgctgctg ctgctgctgc tgctgctgct gctgctgctg   240
ctgctgctgc tgctgctgct gctgctgctg ctgctgctgc tgctgctgct gctgctgctg   300
ctgctgctgc tgctgctgct gctgctgctg ctgctgctgc tgctgctgct gctgctgctg   360
ctgctgctgc tgctgctgct gctgctgctg ctgctgctgc tgctgctgct gctgctgctg   420
ctgctgctgc tgctgctgct gctgctgctg                                   450

<210> SEQ ID NO 30
<211> LENGTH: 19
<212> TYPE: DNA
<213> ORGANISM: Mus musculus

<400> SEQUENCE: 30
gcagcagcag cagcagcag                                                19

<210> SEQ ID NO 31
<211> LENGTH: 19
<212> TYPE: DNA
<213> ORGANISM: Mus musculus

<400> SEQUENCE: 31
gagcagcagc agcagcagc                                                19

<210> SEQ ID NO 32
<211> LENGTH: 19
<212> TYPE: DNA
<213> ORGANISM: Mus musculus

<400> SEQUENCE: 32
ggcagcagca gcagcagca                                                19

<210> SEQ ID NO 33
```

```
<211> LENGTH: 26
<212> TYPE: DNA
<213> ORGANISM: Mus musculus

<400> SEQUENCE: 33
agcagcagca gcagcagcag cagcag                                         26

<210> SEQ ID NO 34
<211> LENGTH: 15
<212> TYPE: DNA
<213> ORGANISM: Mus musculus

<400> SEQUENCE: 34
cagcagcagc agcag                                                     15

<210> SEQ ID NO 35
<211> LENGTH: 15
<212> TYPE: DNA
<213> ORGANISM: Mus musculus

<400> SEQUENCE: 35
ctgctgctgc tgctg                                                     15

<210> SEQ ID NO 36
<211> LENGTH: 20
<212> TYPE: DNA
<213> ORGANISM: Mus musculus

<400> SEQUENCE: 36
agccagccag ccagccagcc                                                20

<210> SEQ ID NO 37
<211> LENGTH: 15
<212> TYPE: DNA
<213> ORGANISM: Mus musculus

<400> SEQUENCE: 37
ctgctgctgc tgctg                                                     15

<210> SEQ ID NO 38
<211> LENGTH: 20
<212> TYPE: DNA
<213> ORGANISM: Mus musculus

<400> SEQUENCE: 38
agccagccag ccagccagcc                                                20
```

COMPOSITIONS AND METHODS FOR IMPEDING TRANSCRIPTION OF EXPANDED MICROSATELLITE REPEATS

STATEMENT REGARDING FEDERALLY SPONSORED RESEARCH OR DEVELOPMENT

This invention was made with government support under Grant No. OD017865 awarded by the National Institutes of Health. The government has certain rights in the invention.

SEQUENCE LISTING

This application contains a sequence listing filed in ST.25 format entitled "222107-1500 Sequence Listing" created on Oct. 3, 2023 and having 26,793 bytes. The content of the sequence listing is incorporated herein in its entirety.

BACKGROUND OF THE INVENTION

Microsatellite expansion diseases are a class of genetically inherited conditions associated with destabilization and expansion of short repetitive sequences in the genome, which cause pathogenic effects via multiple mechanisms including epigenetic silencing, RNA gain of function, and/or protein gain of function. These diseases, including myotonic dystrophy Types 1 and 2 (DM1, DM2), Fuchs' endothelial corneal dystrophy (FECD), Huntington Disease (HD), C9orf72-ALS/FTD (C9ALS/FTD) and spinocerebellar ataxias (SCAs), are often multi-systemic and can affect the central nervous system, muscle, and the heart. Somatic instability causes repeat expansion throughout the lifetime of an individual, with the most dramatic expansions reaching thousands of nucleotides in length in posmitotic tissues. Cellular toxicity in these diseases occurs partly due to transcription of the expanded repeat tract. For example, in DM1 and DM2 expanded CUG or CCUG repeat RNAs, respectively, sequester Muscleblind-like (MBNL) proteins from their endogenous RNA targets leading to aberrant splicing patterns and altered RNA stability/localization, among other effects. In C9ALS/FTD, expanded $G_4C_2$ and $C_4G_2$ repeat RNAs sequester RNA binding proteins, as well as undergo RAN translation to produce toxic dipeptide polymers ALS is a devastating neurodegenerative disease that is characterized by both upper and lower motor neuron dysfunction, leading to paralysis, respiratory failure, and eventual death. Frontotemporal dementia (FTD) is a type of early onset dementia characterized by degeneration of the frontal and anterior temporal lobes, leading to cognitive deficits, as well as behavior and language abnormalities. The most common genetic cause of ALS and FTD is a $G_4C_2$ hexanucleotide repeat expansion (HRE) in the first intron of C9ORF72. Various disease mechanisms have been proposed to explain disease pathogenesis, including 1) the production of RNA species from sense and anti-sense transcripts containing HREs, which may sequester RNA binding proteins, compromising their functions, as well as 2) dipeptide repeats translated from those RNAs through a non-canonical mechanism that does not require an ATG start codon. A third potential disease mechanism that has been proposed is loss of function of the C9ORF72 transcript, due to decreased levels of the mature mRNA from the expanded allele; however, various lines of evidence suggest that haploinsufficiency does not play a significant role in disease pathology.

A number of approaches have been taken to reduce the abundance of sense and anti-sense transcripts in the context of C9ORF72/ALS/FTD. Antisense oligonucleotides targeting each transcript can reduce RNA foci as well as dipeptide synthesis, resulting in rescue of neuronal phenotypes in cell culture as well as behavioral deficits in mouse models of ALS. More recently, depletion of SUPT4H1 and/or SUPT5H in c9ALS fibroblasts has been demonstrated to reduce transcription of both sense and anti-sense HRE transcripts, as well as poly (GP) dipeptide repeats (DPRs). These genes act as co-factors for RNA polymerase II and were initially shown to be required for transcription of long repeats in the context of Huntington's disease.

Various approaches have been taken to silence toxic RNA or protein in microsatellite expansion diseases, including antisense oligonucleotides, small RNAs, and small molecules. Perturbation to co-factors of RNA polymerase II (RNA Pol II) reduces transcription through expanded repeats in HD and C9ALS/FTD models, and treatment with Actinomycin D at nanomolar doses preferentially impedes transcription of CTG repeats in DM models. A hypothesis is that efficiency of transcription through expanded repeats is decreased relative to non-repetitive sequences. This provides a therapeutic window through which to impede transcription of these sequences in a repeat length-dependent manner, resulting in premature termination and nascent transcript turnover.

A deactivated version of the Cas9 enzyme (dCas), of the clustered regularly interspaced short palindromic repeats (CRISPR) system, can be used to impair transcription of specific loci, as well as visualize, tether, and/or isolate DNA in a sequence-specific manner. In prokaryotes, dCas9 efficiently inhibits transcriptional initiation and elongation when bound to gene bodies or promoters. In eukaryotes, dCas9 inhibits transcriptional initiation when fused to an inhibitory domain and targeted near the transcription start site (TSS). However, elongation inhibition by targeting dCas9 alone to the gene body (>1 kb from TSS) has been largely ineffective, even when recruiting dCas9 to >90 possible sites.

SUMMARY OF THE INVENTION

Compositions and methods for treating diseases characterized by expanded microsatellite repeats are disclosed. Disclosed herein are compositions and methods for reducing production of RNA and proteins arising from expanded microsatellite repeats associated with diseases including multiple human diseases, including myotonic dystrophy, Fuchs' endothelial corneal dystrophy, and C9orf72-ALS/FTD.

Systemic delivery of dCas9/gRNA by adeno-associated virus led to reductions in pathological RNA foci, rescue of chloride channel 1 protein expression, and decreased myotonia. These observations suggest that transcription of microsatellite repeat-containing RNAs is more sensitive to perturbation than transcription of other RNAs, indicating potentially viable strategies for therapeutic intervention.

An aspect of an embodiment of the methods includes administering an effective amount of deactivated *S. pyogenes* Cas9 or deactivated *S. aureus* Cas9 to a subject in need thereof. The deactivated Cas9 (dCas9) impedes or inhibits transcription of expanded microsatellite repeats using guide RNAs that directly target the microsatellite repeat tract. A repeat length-, proto-spacer adjacent motif (PAM)-, and strand-dependent reduction of repeat-containing RNAs is achieved upon targeting dCas9 directly to repeat sequences; targeting the non-template strand is preferred. Aberrant splicing patterns are rescued in DM1 cells, and production of repeat associated non-ATG (RAN) peptides characteristic of DM1, DM2, and C9orf72-ALS/FTD cells is drastically decreased.

An aspect of an embodiment of the methods includes administering an effective amount of a small molecule therapeutic that impedes or inhibits transcription of expanded microsatellite repeats to a subject in need thereof. Small molecule therapeutics that impede or inhibit transcription of expanded microsatellite repeats include, but are not limited to, actinomycin D, echinomycin and mythramycin A.

Diseases characterized by expanded microsatellite repeats include myotonic dystrophy type 1, myotonic dystrophy type 2, C9ALS/FTD, spinocerebellar ataxias, Fuch's endothelial corneal dystrophy and other neurological disorders.

An aspect of an embodiment of the compositions of matter that impedes or inhibits transcription of expanded microsatellite repeats includes an AAV vector, AAV virion or AAV viral particle that contains dCas9 and gRNA.

Disclosed herein are: 1) application of CRISPRi to block transcription of HREs in vitro and in vivo, 2) identification of small molecules that block sense and/or antisense transcription of HRE-containing C9ORF72, and 3) characterization of phenotypic changes in C9ALS mice before and after transcriptional blockade.

HA-tagged Cas9 (green) is predominantly nuclear, but also found in the cytoplasm at lower levels. Nuclei are shown in blue. C) and D) are graphs of the analysis of gene expression changes between non-DM1 myoblasts treated with AAV-dSaCas9 and $(CAG)_6$ (SEQ ID NO:1) gRNA and those treated with AAV-dSaCas9 and control gRNA. Genes were grouped by the maximum number of contiguous CTG repeats (C) or CAG repeats (D) found in their pre-mRNA sequences. Numbers of genes found in each group are shown above. Y-axis shows fold-change in log 2 units.

Figure 10:
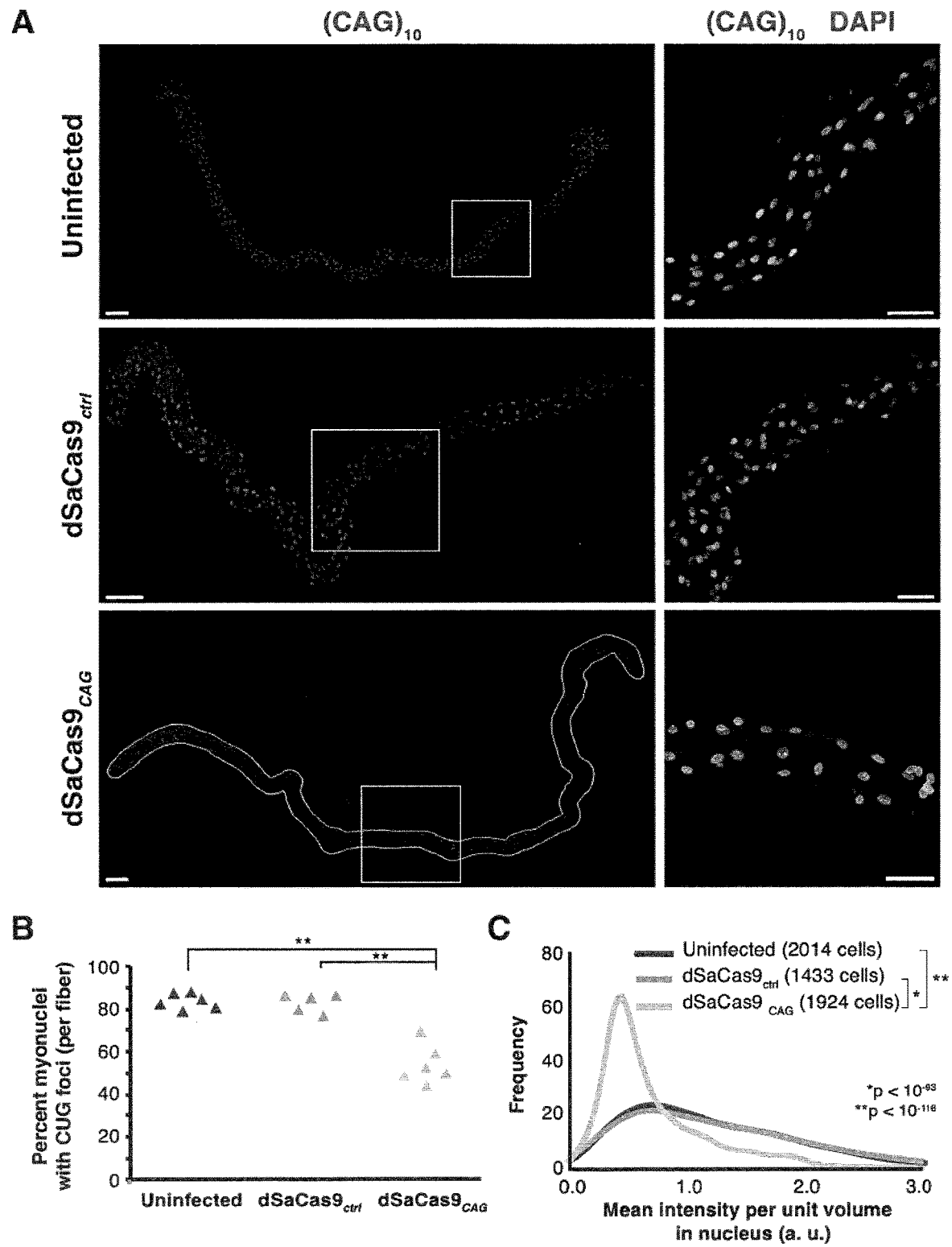
FIGS. 10A-C are photographs and graphs showing that AAV-dSaCas9-(CAG)$_6$ reduces RNA foci in HSA$^{LR}$ muscle fibers. A) is a series of photographs of FISH to detect nuclear RNA foci (magenta) in myonuclei of HSA$^{LR}$ EDL muscle fibers that were untreated (top), infected with AAV-dSaCas9-control gRNA (middle) or (CAG)$_6$ (SEQ ID NO:1) gRNA (bottom). A representative fiber for each condition is shown (Scale bar: 100 μm). Insets from each fiber (white boxes) are on the right (Scale bar: 50 μm). DAPI is in cyan. B) is a graph showing the percentage of myonuclei per fiber showing RNA foci quantitated across all 3 conditions with 5-6 fibers per condition, 400-500 nuclei per fiber (two-tailed T-test, **p<0.0005). C) is a graph of the probability density function of intensity of FISH signal in myonuclei from untreated fibers (red), fibers infected with AAV-dSaCas9-control gRNA or AAV-dSaCas9-(CAG)$_6$ (SEQ ID NO: 1) gRNA. A Kolmogorov-Smirnov test was performed for statistical significance.
Figure 11:
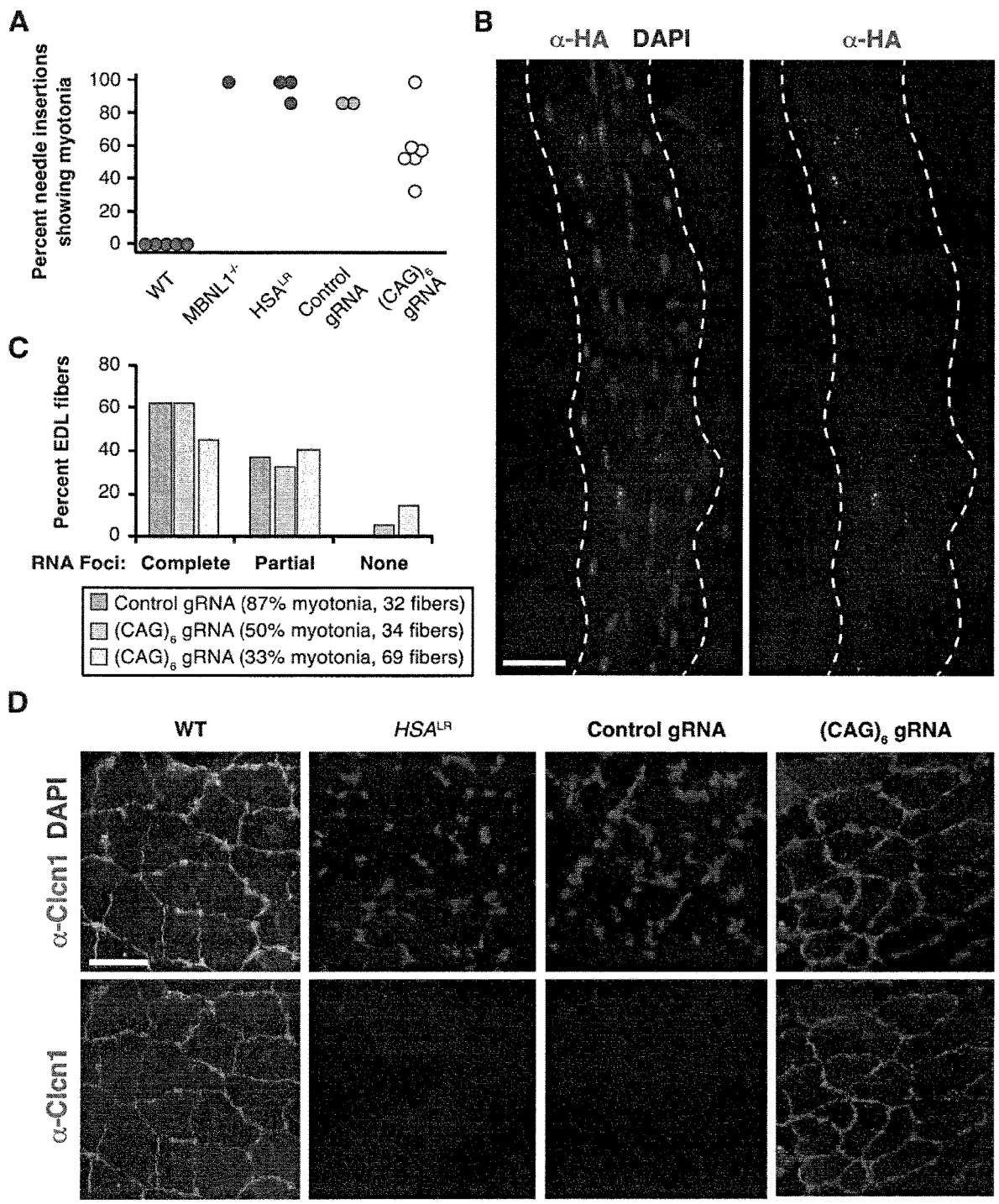
FIGS. 11A-D are photographs and graphs showing that AAV6-dSaCas9-(CAG)$_6$ rescues muscle phenotypes in HSA$^{LR}$ mice. A) is a graph of percent needle insertions showing a myotonic run in wild type FVB, MBNL1$^{-/-}$, HSA$^{LR}$ (black) and HSA$^{LR}$ treated with AAV6-dSaCas9-control gRNA or (CAG)$_6$ (SEQ ID NO:1) gRNA. Each point represents a muscle from a single animal, but in some animals, two muscles were assayed. (p<0.027 for AAV6-dSaCas9-control versus AAV6-dSaCas9-CAG$_6$ treated animals, two-tailed T-test) B) is photographs of IF against HA-dSaCas9 (green) in an EDL fiber from a mouse treated with AAV6-dSaCas9-(CAG)$_6$ (SEQ ID NO: 1) gRNA. DAPI is in blue Scale bar: 50 μm. C) is a bar graph showing quantitation of EDL fibers with complete, partial, or no CUG RNA foci upon treatment with AAV6-dSaCas9-control or (CAG)$_6$ (SEQ ID NO: 1) gRNA. Myotonia levels and numbers of fibers analyzed are also listed. D) is a series of photographs showing IF against Clcn1 in TA muscle sections from FVB, HSA$^{LR}$ and HSA$^{LR}$ treated with AAV-dSaCas9-control or (CAG)$_6$ (SEQ ID NO:1) gRNA. DAPI is shown in blue. Scale bar: 50 μm.

FIGS. 16A-E are photographs and graphs showing the computational analysis of foci intensity in muscle fibers, and experiments to confirm even staining across muscle sections. Related to FIGS. 10-11. A) is a diagram used to minimize computational processing of images, regions of interest were first defined in ~1000×1000×100 blocks. B) is a series of photographs and a graph showing that nuclei were segmented using standard image processing techniques. Images were smoothed with a Gaussian filter, thresholded, and segmented for nuclei. C) is a series of photographs and graphs showing that FISH signal was similarly processed. Background was subtracted, and FISH signal within nuclei was quantitated by applying the nuclei mask from (B). Also see Examples. D) is a graph of percent needle insertions showing a myotonic run in wild type FVB, $MBNL1^{-/-}$, $HSA^{LR}$, (black circles) and $HSA^{LR}$ treated with AAV9-dSaCas9 with control gRNA (orange circles) or $(CAG)_6$ gRNA (yellow circles). Each point represents a muscle from a single animal, but in some animals, both tibialis anterior and gastrocnemius were assayed. N=4 mice for control gRNA and N=4 mice for $(CAG)_6$ (SEQ ID NO:1) gRNA. E) is photographs showing immunofluorescence performed against lamin A using an anti-lamin A antibody on mouse EDL muscle fibers, showing uniform detection of lamin A in myonuclei along the length of the fiber.

DETAILED DESCRIPTION OF THE INVENTION

Expanded microsatellite repeats are highly sensitive to transcriptional blockade by dCas9, even in the context of elongating RNA Pol II. It was found that efficiency of inhibition follows rules similar to those observed in non-repetitive contexts, with clear dependencies on proto-spacer adjacent motif (PAM) sequence and targeted DNA strand. In addition, application of this approach to cell and animal models of disease rescues downstream pathogenic consequences. These observations describe application of the CRISPR/Cas9 system to impede transcription of expanded microsatellites in a strand-dependent manner, and demonstrate that targeting transcription in a repeat length-dependent manner is a viable therapeutic strategy for these diseases.

Amotrophic lateral sclerosis (ALS) is a devastating disease affecting approximately 1 in 25,000 individuals in the US. The most common genetic cause of ALS is a hexanucleotide G4C2 repeat expansion (HRE) found within the first intron of C9orf72. In addition to motor neuron disease, this repeat can also cause frontotemporal dementia (FTD), at times comorbid with motor neuron disease. The length of the HRE is inversely correlated with age of onset, as well as survival after disease onset. Evidence indicates that both sense (G4C2) and antisense (C4G2) RNAs are transcribed from these repeats, repeat associated non-ATG (RAN) peptides are translated from these RNAs, and that these molecules are toxic to cells. Proof of principle experiments reducing abundance of HRE-containing RNAs have rescued molecular and physiological phenotypes in cell and animal models of C9ALS/FTD, either through using antisense oligonucleotides, or by perturbing co-factors of RNA Polymerase II to elicit elongation failure across HREs.

While these studies suggest that reducing toxic RNA abundance will rescue pathology in C9ALS/FTD, a need exists to establish the relative contribution of sense vs. antisense HRE transcripts to disease, so that the appropriate molecules can be successfully targeted. In the context of therapeutic development, it is critical to characterize molecular events downstream of each transcript species so that potential benefit can be accurately measured. To date, understanding the role of individual transcripts in disease has been technically difficult due to challenges in targeting individual transcripts, and the need for an animal model that express both sense and antisense transcripts, and exhibits robust phenotypes mirroring the human disease. To address these challenges, deactivated (d) Cas9 with HRE-targeting guide RNAs are being used to inhibit transcription of expanded microsatellite repeats in a strand-specific manner (CRISPRi). A BAC-transgenic mouse model of C9ALS/FTD has been developed that recapitulates bidirectional transcription and the severe neurodegenerative phenotypes of the human disease, including loss of upper and lower motor neurons. This mouse model and other cell-based models of ALS will be used to 1) characterize the molecular pathophysiology downstream of sense and antisense repeat transcription, 2) evaluate the therapeutic impact of dCas9-mediated transcriptional blockage of one or both transcripts, and 3) identify small molecules that block sense and/or antisense transcription in cell and animal models of C9ALS/FTD.

A deactivated form of the clustered regularly interspaced short palindromic repeats (CRISPR) system has been shown to efficiently block transcription, either by tethering transcriptional inhibitory domains to eukaryotic promoters, or alone, without any additional protein cargo, in bacteria (CRISPR inhibition, CRISPRi). Expanded microsatellite repeats present significant challenges for elongating eukaryotic RNA polymerase II, and targeting deactivated Cas9 to repeats could block transcription of repeats much more efficiently than other loci lacking such long contiguous repeats. In preliminary studies, efficient blockade of expanded CTG, CCTG, and $G_4C_2$ transcription was demonstrated, as assayed by RNA abundance as well as RAN protein production.

CRISPRi will be used to validate transcriptional inhibition as a therapeutic approach for C9ALS, downstream consequences of blocking sense versus anti-sense transcription will be evaluated, and small molecules will be identified that can efficiently, yet selectively impede transcription of HREs. A previous limiting factor in C9ALS therapeutic studies was the availability of a mouse model recapitulating human disease phenotypes, in particular lower motor neuron phenotypes. A BAC-based model fulfilling this need has recently been developed, and it will be used to measure changes in disease pathology upon blocking sense and/or antisense transcription.

Figure 7:
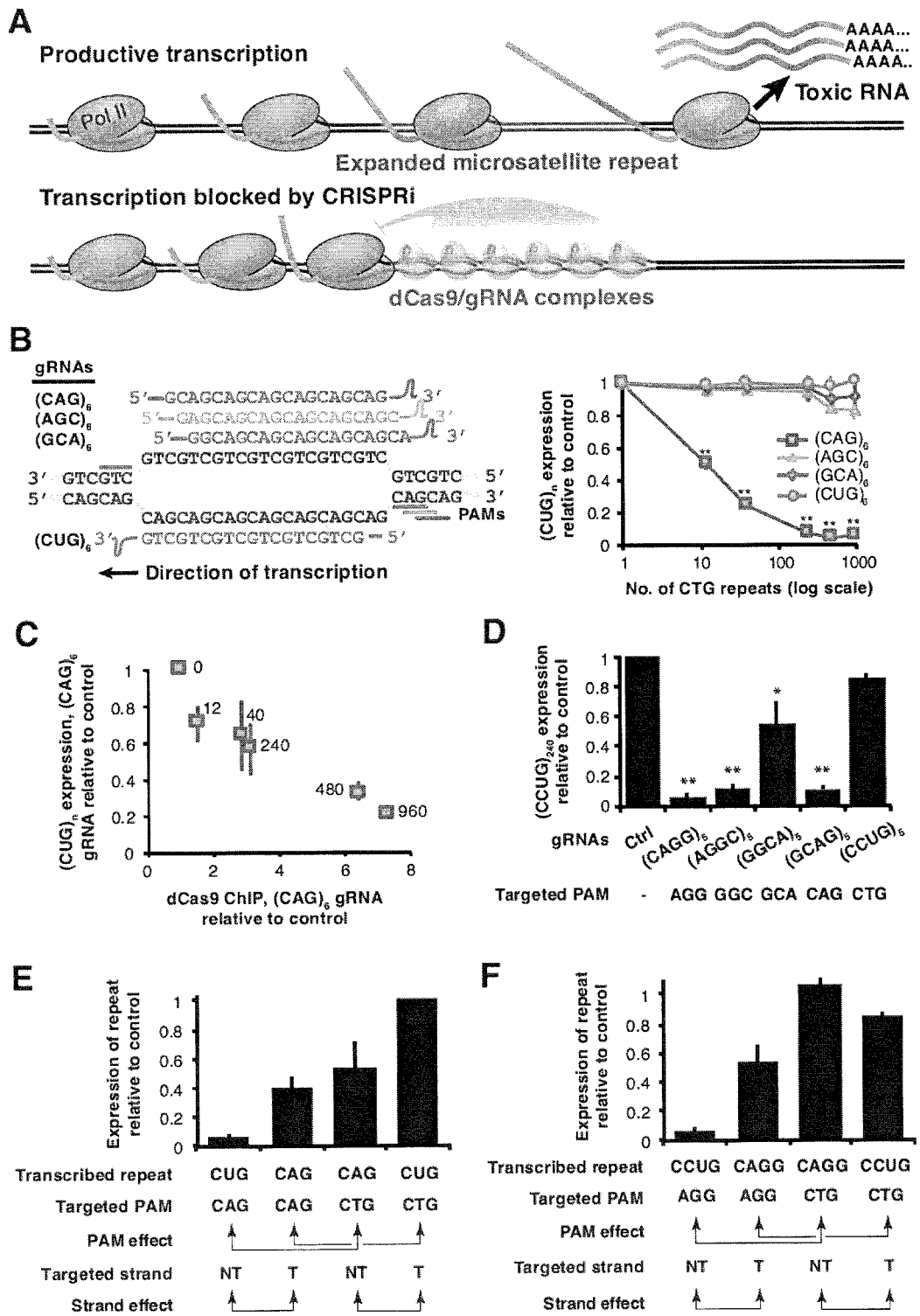
FIGS. 7A-F are diagrams and graphs showing that deactivated SpCas9 impedes transcription of expanded microsatellite repeats in a length-, PAM-, and strand-dependent manner. A) is a diagram of a proposed model for how recruitment of dCas9/gRNA complexes to expanded microsatellite repeats impedes transcription by RNA Pol II B) is a schematic (left panel) and graph (right panel) of gRNAs $(CAG)_6$ (SEQ ID NO:1), $(AGC)_6$ (SEQ ID NO:4), $(GCA)_6$ (SEQ ID NO:5), or $(CUG)_6$ (SEQ ID NO:3) used to target transcription of CTG repeats (left panel) (shown are SEQ ID NOs: 30-33). Abundance of CUG repeat RNA in the presence of dCas9/gRNAs targeting the repeat tracts of various lengths in HeLa cells, relative to the same RNA species with zero repeats (right panel). Error bars show standard deviation. C) is a graph showing relative dCas9 ChIP signal across all repeat lengths versus percent RNA remaining following $(CAG)_6$ (SEQ ID NO:1) gRNA relative to control gRNA treatment. dCas9 ChIP signal is computed as dCas9 IP divided by input chromatin with $(CAG)_6$ (SEQ ID NO:1) gRNA treatment, divided by dCas9 IP divided by input chromatin with control gRNA treatment. Relative abundance of repeat-containing loci and RNAs was assessed by deep sequencing of the barcodes. Error bars show standard error of the mean. D) is a bar graph showing abundance of CCUG repeat RNA in the presence of dCas9 and gRNAs $(CAGG)_5$ (SEQ ID NO:6), $(AGGC)_5$ (SEQ ID NO:7), $(GGCA)_5$ (SEQ ID NO:8), and $(CCUG)_5$ (SEQ ID NO:15) targeting the $(CCTG)_{240}$ (SEQ ID NO:14) repeat tract in Hela cells, relative to the same RNA species with zero repeats. E) is a bar graph showing abundance of RNAs containing 960 CUG or CAG repeats (SEQ ID) NOs: 24 and 21, respectively) in the presence of dCas9 and $(CUG)_6$ (SEQ ID NO:3) or $(CAG)_6$ (SEQ ID NO: 1) gRNAs in HeLa cells, relative to RNA species with zero repeats. Arrows denote comparisons relevant for assessing PAM- or strand-dependent effects on efficacy. F) is a bar graph showing abundance of RNAs containing 240 CCUG or CAGG repeats (SEQ ID NOs: 19 and 22, respectively) in the presence of dCas9 and $(CCUG)_5$ (SEQ ID NO: 15) or $(CAGG)_5$ (SEQ ID NO:6) gRNAs in Hela cells, relative to RNA species with zero repeats. Arrows denote comparisons relevant for assessing PAM- or strand-dependent effects on efficacy. (All significance tests are by two-tailed T-test, **p<0.0005, *p<0.005)
Figure 12:
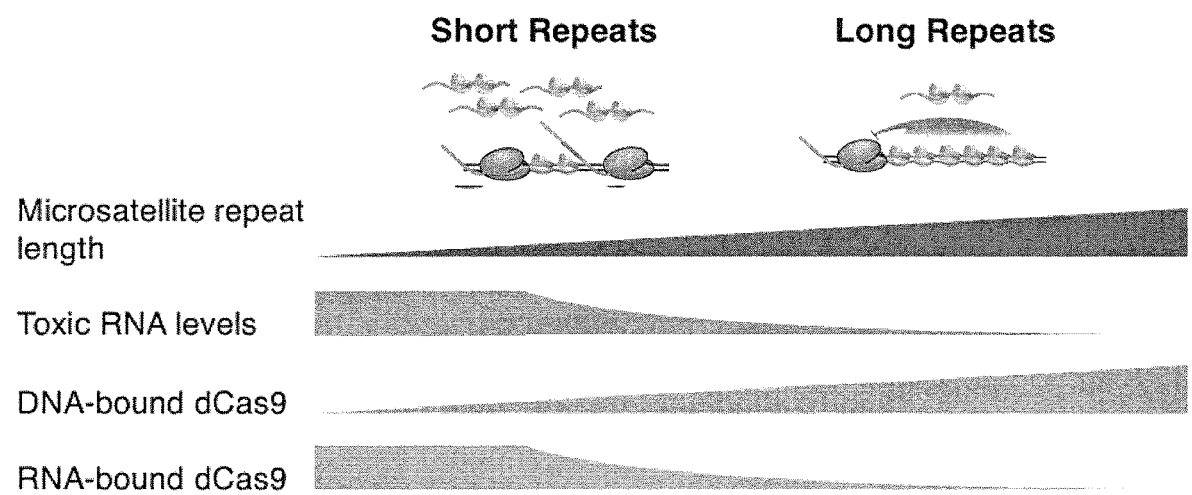
FIG. 12 is a diagram of a model for microsatellite repeat expansion targeting by dCas9. dCas9 binding to DNA impedes transcription of long, expanded microsatellite repeats. In the context of shorter repeats, fewer copies of DNA-bound dCas9 may be insufficient to fully inhibit elongation by RNA Pol II, permitting production of RNA that can also be targeted by dCas9.
Figure 14:
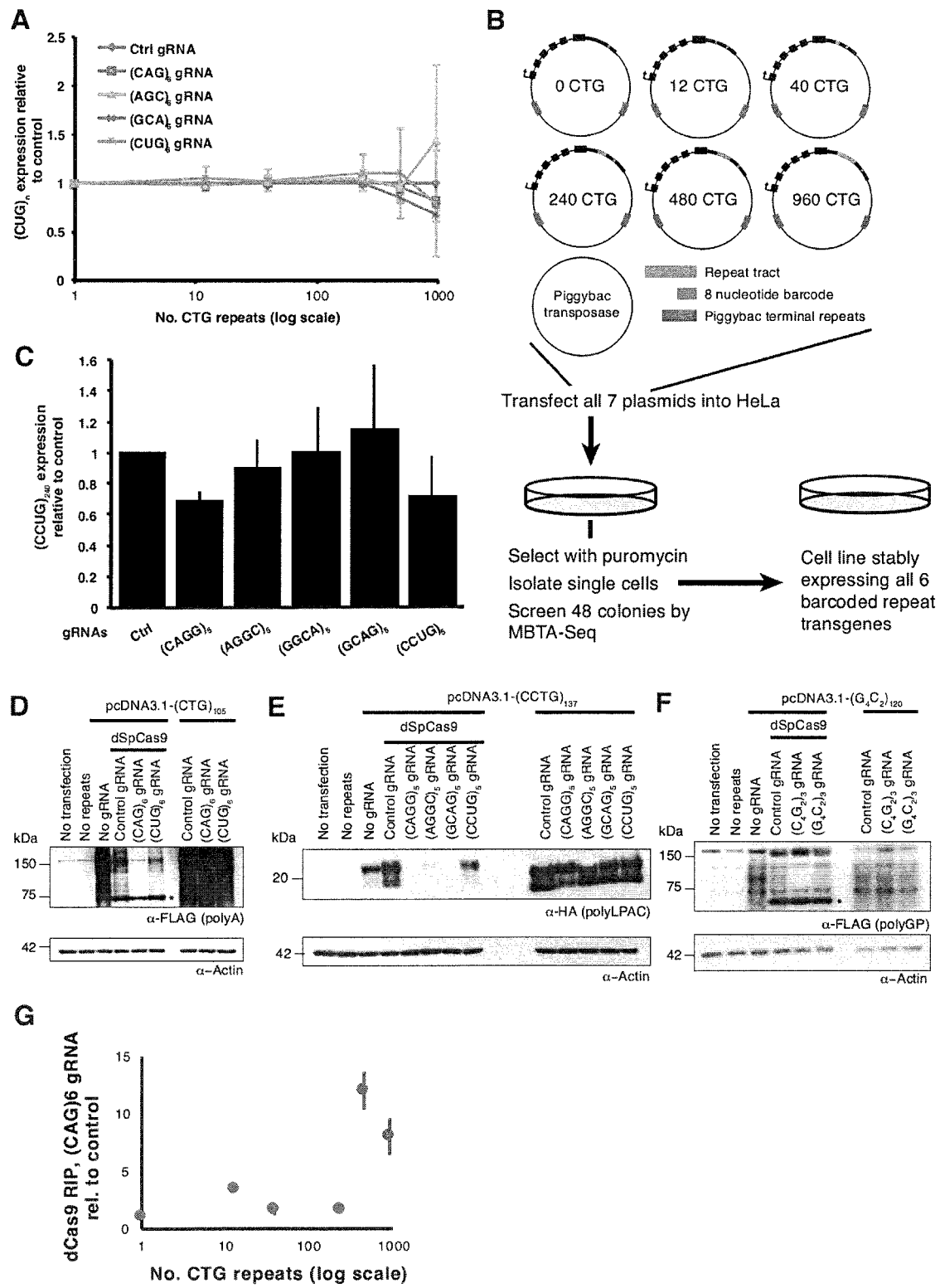
FIGS. 14A-G are graphs, diagrams and photographs showing that gRNA alone without dCas9 does not significantly affect levels of expanded microsatellite repeat transcript and RAN translated products. Related to FIGS. 7-8. A) is a graph showing abundance of CUG repeat-containing RNA in the presence of various gRNAs targeting CTG repeat tracts of various lengths, relative to abundance of RNA with no CUG repeats. B) is a diagram of the procedure to establish stable cell line that simultaneously expresses transcripts containing 0, 12, 40, 240, 480, and 960 CTG repeats, with associated 8 nucleotide-long barcodes. Plasmids were subcloned into plasmids with Piggybac terminal repeats, which facilitate genomic integration when co-expressed with the Piggybac transposase. All repeat transcripts are driven by EF1α promoter, and plasmids also contain a PGK promoter-driven puromycin cassette. HeLa cells were transfected with all 7 plasmids, selected by puromycin, and sorted for single cells by flow cytometry. 48 clones were isolated and screened by MBTA-Seq. 2 cell lines were successfully identified to contain all 6 repeat transcripts. C) is a bar graph showing the abundance of CCUG repeat-containing RNA in the presence of various gRNAs targeting the (CCTG)$_{240}$ (SEQ ID NO:14) repeat tract, relative to abundance of RNA with no CCUG repeats. D) is a photograph of a Western blot analyses of the poly-Ala RAN translated product (FLAG-tagged) expressed from DM1 (CTG)$_{105}$ (SEQ ID NO:17) repeats transfected into HEK293T cells. Cells were transfected with plasmids carrying no repeats or (CTG)$_{105}$ (SEQ ID NO:17) repeats and combinations of control, (CAG)$_6$ (SEQ ID NO: 1) or (CUG)$_6$ (SEQ ID NO:3) gRNAs with and without dCas9. The RAN product migrates as a smear between 75 and 150 kD. E) is a photograph of a Western blot against the poly-LPAC RAN translated product (HA-tagged) expressed from DM2 (CCTG)$_{137}$ (SEQ ID NO:18) repeats transfected into HEK293T cells. Cells were transfected with no repeats or (CCTG)$_{137}$ (SEQ ID NO:18) repeats and combinations of control, (CAGG)$_5$ (SEQ ID NO:6), (AGGC)$_5$ (SEQ ID NO:7), (GCAG)$_5$ (SEQ ID NO:9) or (CCUG)$_5$ (SEQ ID NO: 15), gRNAs with and without dCas9. The RAN translated product runs at around 20 kD. F) is a photograph of a Western blot against the poly-GP RAN translated product (FLAG-tagged) expressed from C9orf72-ALS/FTD (G$_4$C$_2$)$_{120}$ (SEQ ID NO:20) repeats transfected into HEK293T cells. Cells were transfected with plasmids carrying no repeats or (G$_4$C$_2$)$_{120}$ (SEQ ID NO:20) repeats and combinations of control, (C$_4$G$_2$)$_3$ (SEQ ID NO:10) or (G$_4$C$_2$)$_3$ (SEQ ID NO:11) gRNAs with and without dCas9. The RAN product migrates as a smear between 75 and 120 kD. The asterisk indicates protein produced by the dSpCas9 plasmid, which cross-reacts with the anti-FLAG antibody. β-Actin serves as the loading control for D, E and F. N=3 for D, E, and F (representative blot shown). G) is a graph showing that dCas9 RIP was performed to quantitate the relative abundance of various repeat-containing transcripts bound by dCas9, using the cell line described in panel (B). Anti-HA antibody was used to immunoprecipitate dCas9 in cells treated with control gRNA or (CAG)$_6$ (SEQ ID NO: 1) gRNA. RNA was isolated from total lysate, or from the immunoprecipitation. The relative enrichment is plotted as a function of repeat length, e.g. (CAG)$_6$ (SEQ ID NO:1) gRNA IP divided by (CAG)$_6$ (SEQ ID NO:1) gRNA input, divided by control gRNA IP divided by control gRNA input.

CRISPR/Cas9 has been previously applied to microsatellite expansion diseases, to remove expanded repeat tracts or to cause repeat contraction. Here a deactivated form of Cas9 was applied to these diseases. By testing disease-associated repeat sequences across multiple repeat lengths in vitro and in disease models, it was demonstrated that dCas9 can substantially reduce repeat-containing transcript abundance. Importantly, repression efficiency is proportional to repeat length, because longer repeats recruit an increased number of dCas9/gRNA complexes, leading to greater transcriptional blockade (FIG. 7B-C).

dCas9 is well established to target DNA, but has also been shown to bind repeat-containing RNA in a gRNA-dependent manner. Indeed, when dCas9 was immunoprecipitated and RNA binding was assessed, increased binding to transcripts containing longer repeats was observed (FIG. 14G). However, as repeat length increases, the amount of successfully transcribed RNA decreases, suggesting that at long repeat lengths, less RNA remains to be targeted. In the context of disease, microsatellite repeat tracts undergo dramatic somatic expansion in DM1, DM2, C9ALS/FTD, and HD, and evidence suggests that repeat lengths in tissues of symptomatic individuals reach thousands of nucleotides in length. Therefore, DNA-based targeting by dCas9 may play a primary role in driving potential therapeutic benefits in individuals with full expansions (FIG. 12). At short and intermediate repeat lengths, therapeutic benefit may derive from both DNA- and RNA-based targeting by dCas9, to not only impede transcription of repeat-containing DNA, but also modulate downstream consequences of transcribed "escaper" RNAs. Taken together, it was demonstrated that dCas9 is an effective tool to limit downstream effects of toxic RNAs.

While this approach mitigates a key safety concern of CRISPR, which is the unwanted cleavage of off-targets, it raises questions about whether long-term exposure to dCas9 can be achieved and tolerated. Effective, safe delivery in a multi-systemic fashion to sufficient numbers of post-mitotic cells will be necessary for this approach to be therapeutically viable. In DM and C9ALS/FTD, it is unclear what fraction of nuclei must be rescued in muscle or central nervous system to halt or improve disease symptoms. Here, it was observed that rescue of a subset of nuclei was sufficient to yield partial rescue of myotonia. However, myotonia can be modeled as a loss-of-function event in which Clcn1 protein is lost, and there is evidence that in other recessive muscle diseases, gene editing of a small subset of nuclei can restore sufficient protein expression across muscle fibers to yield therapeutic benefit. Conversely, mis-splicing events yielding pathogenic isoforms with dominant-negative behavior may require full elimination to mitigate deleterious consequences.

Systemically delivered AAV was used, which revealed regional variation in transduction efficiency, likely because NLS-tagged Cas9 protein remained restricted to myonuclear domains transduced by AAV episomes, and many new myonuclei are recruited to fibers throughout postnatal muscle development. Previous studies with AAV-mediated gene therapy typically evaluate expression of proteins that can spread throughout muscle fibers, precluding measurement of transduction efficiency to all myonuclei. It is possible that localized delivery would have facilitated transduction of a higher proportion of myonuclei. Nevertheless, reduction of toxic RNA repeat load in a subset of nuclei was sufficient to increase production of Clcn1 protein, with consequences for distant regions of muscle potentially naïve to dCas9. These results emphasize how differences in mechanism of action and delivery efficiency between various therapeutic approaches should significantly influence how changes in response to those therapies are interpreted, both at the molecular and phenotypic level.

In summary, the ability of dCas9 to impede transcription of microsatellite expansions defines a window in which transcriptional inhibition of expanded repeats is feasible, yet does not interfere with that of typical RNAs. This approach serves as a baseline with which to compare alternative therapeutic approaches, as well as a tool to identify mechanisms and principles by which transcriptional activity of RNA polymerase II can be modulated in a sequence-specific manner.

Figure 1:
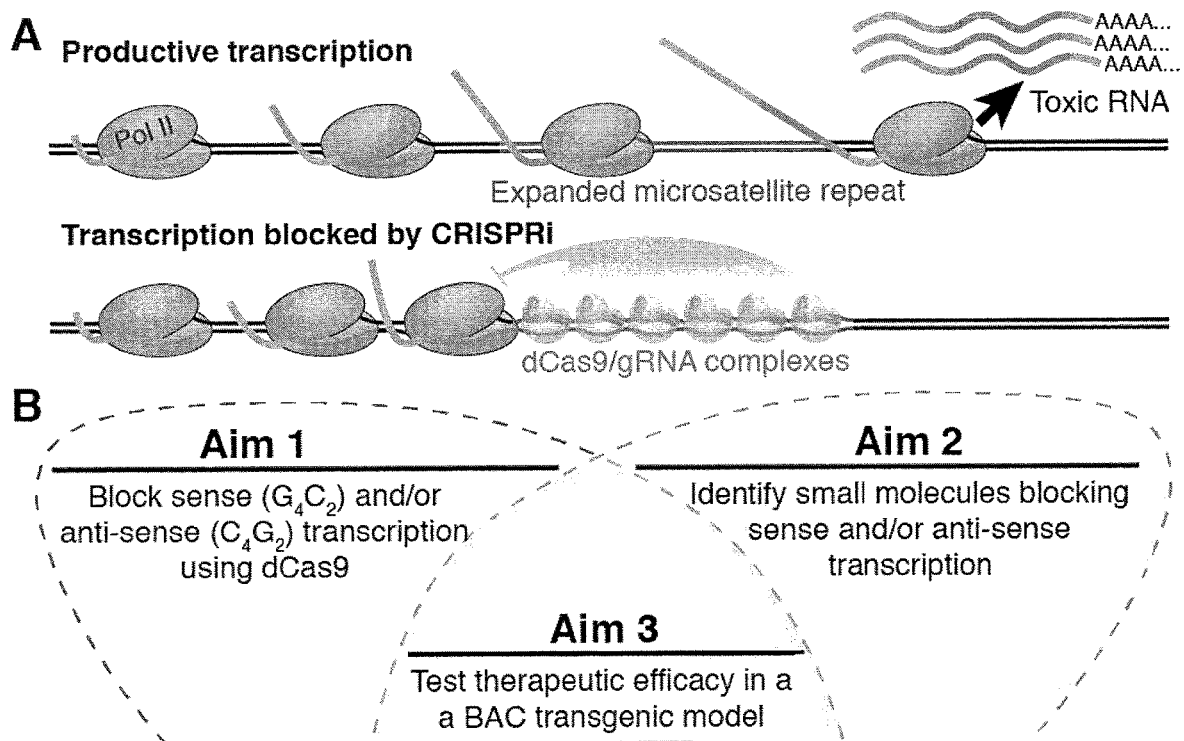
FIG. 1A is a depiction of the strategy of the methods of the invention using deactivated Cas9 to block transcription of HREs. The large number of dCas9/guide RNA complexes bound to DNA can impede transcription in a strand-specific manner.
FIG. 1B is a diagram showing identifying small molecules that impede HRE transcription, and testing CRISPRi and small molecules in a mouse model of ALS.
Figure 2:
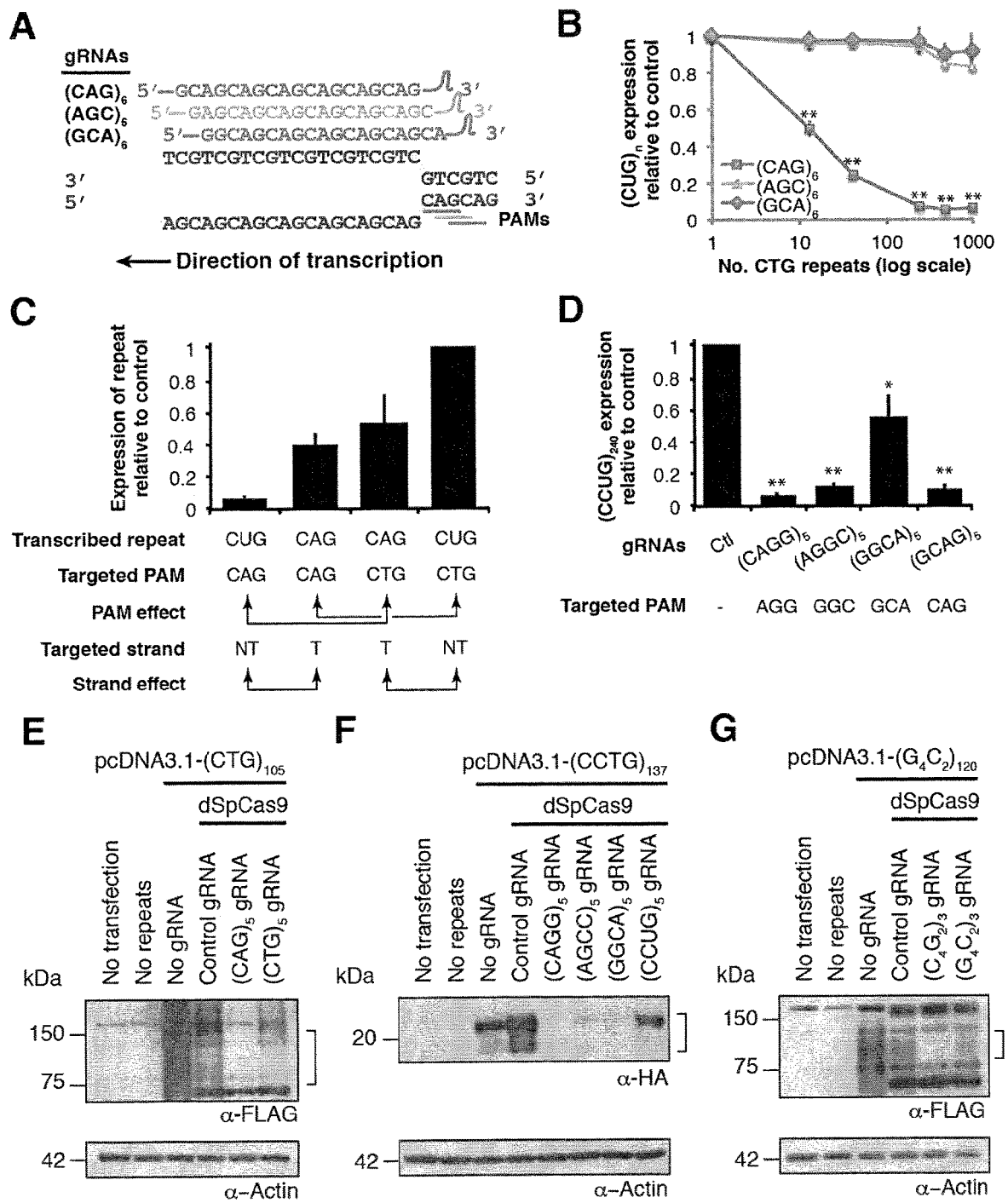
FIGS. 2A-G are graphs and photographs showing that dCas9 impedes transcription of expanded repeats. A) is a schematic of gRNA/DNA hybridization for 3 different gRNAs targeting CTG repeats (shown are SEQ ID NOs: 30-33). B) is a graph showing expression of CUG repeat-containing RNA in the presence of dCas9 and gRNAs targeting repeats. Length-dependent reduction in expression is achieved with the $(CAG)_6$ (SEQ ID NO:1) gRNA but not the $(AGC)_6$ (SEQ ID NO:4) or $(GCA)_6$ (SEQ ID NO:5) gRNA. C) is a bar graph showing expression of repeat relative to control. Plasmids encoding 960 CTG or CAG repeats were assayed for expression in the presence of $(CAG)_6$ (SEQ ID NO:1) gRNA or $(CTG)_6$ (SEQ ID NO: 2) gRNA. The CAG PAM suppresses more effectively than CTG, and targeting the non-template strand is more effective than targeting the template strand. D) is a bar graph showing that DM2 CCTG repeats can be effectively suppressed by guide RNAs encoding CAGG repeats. E)-G) are photographs of Western blots showing that dCas9 and gRNAs suppress RAN translation of CTG (E), CCTG (F) and $G_4C_2$ (G) repeats, as assayed using protein tags in frame with RAN peptides. Shown are $(CAGG)_5$ (SEQ ID NO:6), $(AGGC)_5$ (SEQ ID NO:7), $(GGCA)_5$ (SEQ ID NO:8), $(GCAG)_5$ (SEQ ID NO:9), $(CAG)_5$ (SEQ ID NO:34), $(CTG)_5$ (SEQ ID NO:37), $(AGCC)_5$ (SEQ ID NO:38), $(CCUG)_5$ (SEQ ID NO:15), $(C_4G_2)_3$ (SEQ ID NO:10), and $(G_4C_2)_3$ (SEQ ID NO:11).

CRISPRi was used to block transcription of expanded microsatellite repeats. Deactivated Cas9 has been demonstrated to work most efficiently when fused to a transcriptional inhibitory domain (e.g., KRAB domain), and targeted by a guide RNA close to the transcriptional initiation site. However, because Pol II elongates less efficiently through expanded microsatellite repeats potentially due to alternative DNA structures, transcription could be impeded by targeting multiple copies of dCas9 to the repeat tract using a repeat-targeting guide RNA. A plasmid-based systems in cell culture was used to test this approach, and effective transcriptional blockade of expanded CTG repeats (myotonic dystrophy type 1), CCTG repeats (myotonic dystrophy type 2), and G4C2 repeats was observed. In the context of DM1 repeats, knockdown is most efficient with a protospacer-adjacent motif (PAM) of CAG, then AGC, and finally GCA, consistent with PAM efficacy (NGG >NAG >NCG >NTG)[16] (FIG. 2A-B). Also, targeting of expanded CTG repeats using a $(CAG)_6$ (SEQ ID NO: 1) gRNA is much more effective than targeting expanded CAG repeats using a $(CTG)_6$ (SEQ ID NO:2) gRNA (FIG. 2C), consistent with the previous observation that inhibiting Pol II via gRNA binding to the non-template strand is more effective than gRNA binding to the template strand, likely due to helicase activity of Pol II on the template strand. Similar suppression of transcription is observed with expanded CCTG/CAGG repeats (FIG. 2D). RAN translation of CTG, CCTG, and $G_4C_2$ repeats is also suppressed in a dCas9 and gRNA-dependent manner (FIG. 2E-G). Serendipitously, at least for Cas9 variants *Streptococcus pyogenes* and *Staphylococcus aureus*, effective targeting of both sense and antisense transcripts can be achieved because the $G_4C_2$ HRE sequence contains optimal PAMs on both strands. We should be able to preferentially block sense transcription using a $(C_4G_2)_3$ gRNA, or antisense transcription using a $(G_4C_2)_3$ (SEQ ID NO:11) gRNA. Indeed, RAN protein produced from transfected plasmids encoding $(G_4C_2)_{120}$ (SEQ ID NO:20) is blocked effectively by $(C_4G_2)_3$ (SEQ ID NO:10) gRNA, but not as effectively by $(G_4C_2)_3$ (SEQ ID NO:11) gRNA (FIG. 2G).

For studies with difficult-to-transfect cell types, as well as in animal tissues, *S. aureus* dCas9 and gRNAs have been packaged into a single adeno-associated virus (AAV), and high infectivity in human myoblasts and dissected mouse muscle fibers in culture was observed. A reduction in RNA foci was observed, and rescue of mis-splicing in DM1 was observed. In a similar approach for C9ALS/FTD, dCas9 and either a $G_4C_2$ repeat-targeting gRNA or a $C_4G_2$ repeat-targeting gRNA will be packaged in AAV. Assays will be run for reduction of RNA foci and RAN protein in C9ALS/FTD patient-derived fibroblast and lymphoblastoid cells. Then, in vivo assays will be performed in a mouse model, which exhibits both upper and lower motor neuron deficits. Then sense/antisense RNA foci will be measured, RAN protein production will be measured, other histopathological abnormalities characteristic of human C9ALS/FTD will be measure, and physiological phenotypes will be observed. The recently described viral capsids, PHP.A and PHP.B, that can efficiently transduce the central nervous system, including neurons, glia, and oligodendrocytes of the brain and spinal cord via intravenous injection will be used.

Figure 3:
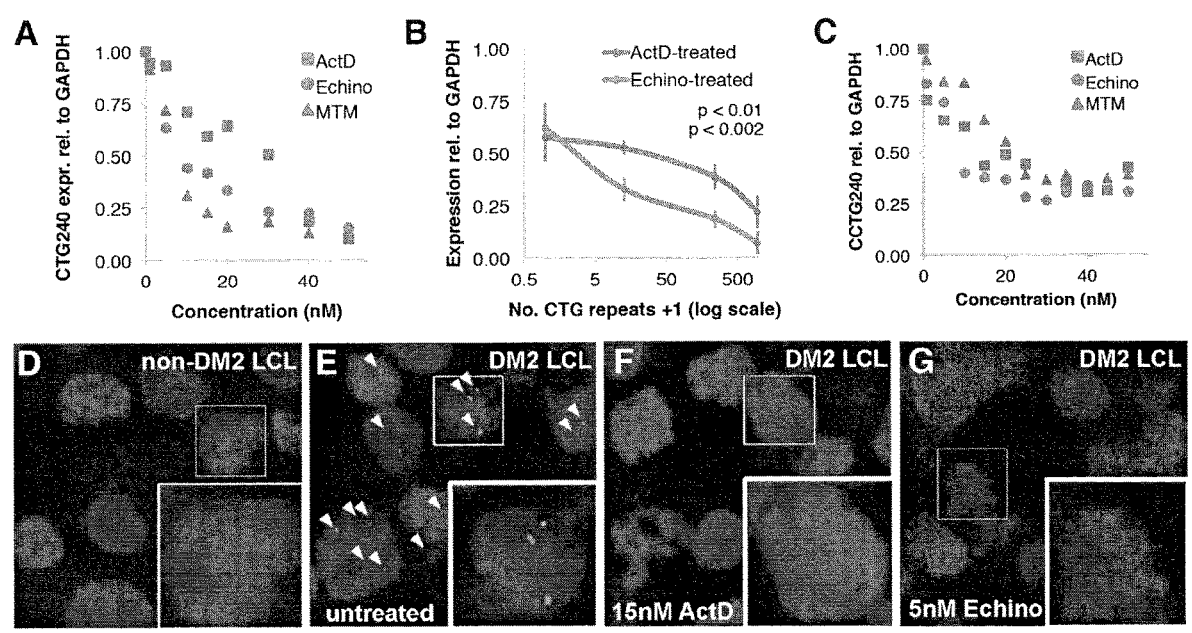
FIGS. 3A-G are graphs and photographs showing that small molecules impede transcription through expanded CTG/CCTG repeats. A) is a graph showing that three different molecules, actinomycin D (ActD), echinomycin (Echino) and mythramycin A (MTM), impede transcription of CTG240 relative to GAPDH in a concentration-dependent manner. B) is a graph showing that ActD and Echinomycin inhibit transcription of CTG repeats in a repeat length-dependent manner. C) is a graph showing that the three different molecules impede transcription of CCTG240 relative to GAPDH in a concentration-dependent manner. D-G) show RNA foci appear in DM2 lymphoblastoid cells (LCL) but not non-DM2 LCLs, and are reduced when treated with ActD or Echinomycin.

Small molecules were identified that impede transcription of HREs. Although the dCas9/gRNA system could be developed into a gene therapy, there are delivery challenges associated with such a treatment. Therefore, small molecules will be identified that can impede transcription through HRE-containing transcripts. In the DM field, FDA-approved compounds have been identified that can specifically reduce the abundance of CTG and/or CCTG repeat-containing transcripts. For example, at low nanomolar doses, the global transcriptional inhibitor Actinomycin D (ActD) can preferentially impede transcription of expanded CTG repeats; this leads to a reduction in CUG repeat-containing RNA, release of the Muscleblind-like RNA binding proteins, and rescue in RNA mis-splicing in a mouse model of DM18. Additional FDA-approved compounds have been identified that may inhibit transcription of GC-rich sequences, and their efficacy in reducing CTG/CCTG repeat transcription was tested (FIG. 3). Several compounds do so in a concentration- and repeat length-dependent manner, as measured by RT-qPCR relative to GADPH, as well as by presence of RNA foci in patient cell lines. It will be determined whether the compounds shown in FIG. 3 also inhibit transcription of $G_4C_2$ and $C_4G_2$ repeats, as well as adapt a high throughput screen that was developed for DM1 CTG repeats to HREs. In brief, a HeLa nuclear extract is used to transcribe repeat-containing transcripts and relevant control transcripts in vitro, and conditions are adjusted to measure abundance of newly transcribed RNA using multiplex RT-qPCR. This system will be adapted so that HREs are transcribed instead of CTG repeats, and FDA-approved compound libraries (e.g., LOPAC) will be screened, as well as additional proprietary libraries. These experiments will synergize with experiments in the context of DM1 and DM2-specifically, compounds may be identified that successfully impede transcription of all expanded repeats, or different compounds whose differential inhibitory activity may be identified that will enlighten the structure-function relationships for multiple repeat sequence types. Compounds identified will be tested for activity and toxicity in C9ALS/FTD fibroblasts and iPS-derived neurons. If these compounds are active in cells and have low toxicity, they will then be tested in the BAC-based mouse model described below.

Figure 4:
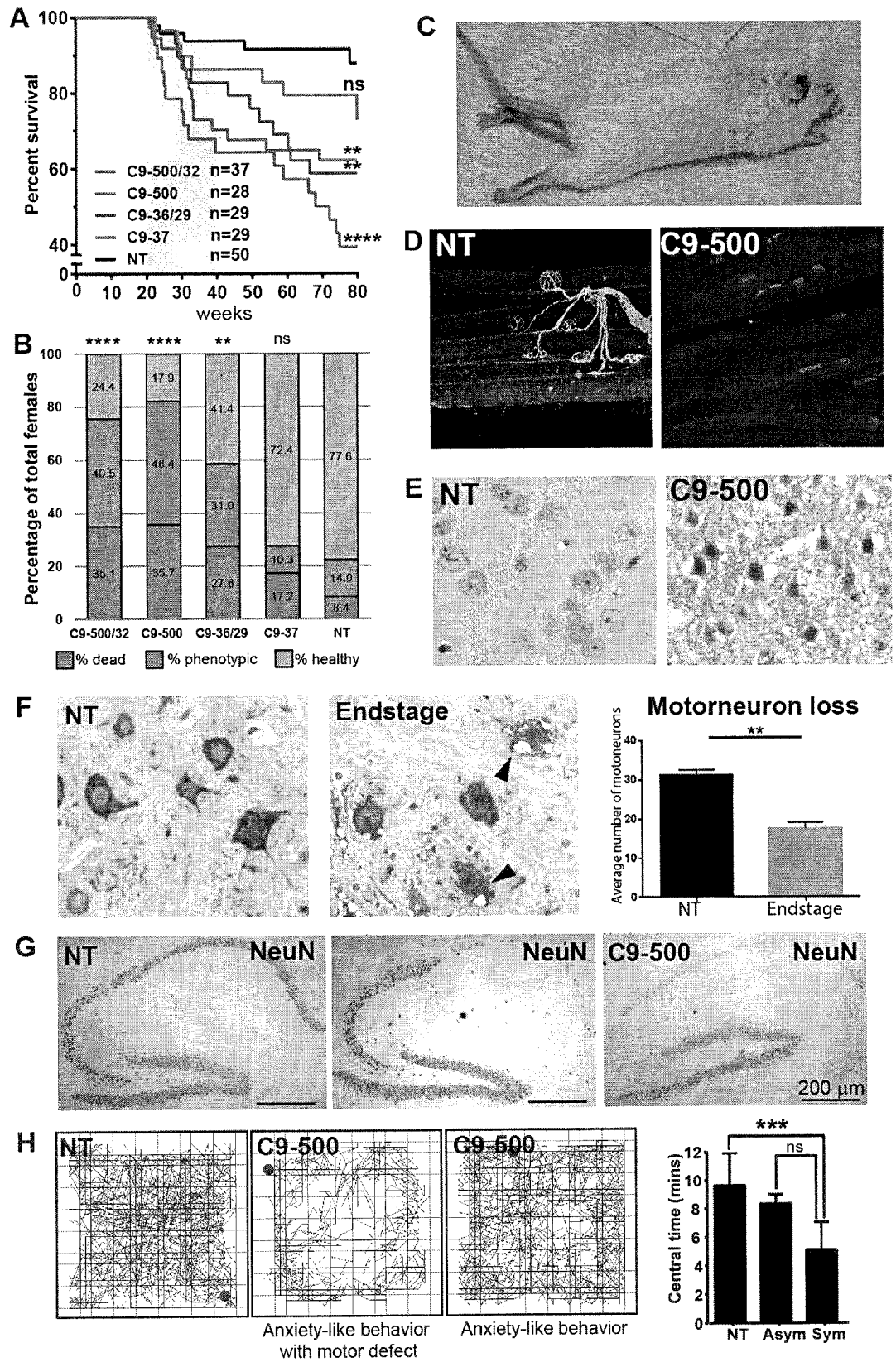
FIGS. 4A-H are graphs and photographs showing features of C9-BAC mice. A) is a graph showing reduced survival, B) is a bar graph showing that 82% are phenotypic at 1 year, C) is a photograph showing paralysis, D) is photographs showing neuromuscular junction denervation, E) is photographs showing neurodegeneration of motor cortex, F) is photographs and a bar graph showing spinal motor neuron loss, G) is photographs showing hippocampal neuron loss, and H) are plots and a bar graph showing open-field anxiety-like cage behavior.

Changes in a mouse model of C9ALS were characterized. A BAC-based model that recapitulates molecular, neurodegenerative and behavioral changes observed in C9 ALS/FTD patients was developed. Three independent lines, generated using a patient-derived C9ORF72 (+) BAC, develop molecular and clinical features of ALS/FTD in a repeat-length and gene-dose dependent manner, including a single copy line with 500 $G_4C_2$ repeats (C9-500). Both sense and antisense RNA foci accumulate in expansion animals and are found throughout the brain and spinal cord. Additionally, the three symptomatic lines express GA and GP RAN proteins, which accumulate as aggregates in the brain. All three symptomatic lines develop neurological/neuromuscular phenotypes starting at ~4 months including: a) limb paralysis; b) neuromuscular junction denervation; c) neuronal loss in multiple brain regions including spinal-cord lower motor neurons, layers II/III and V of the motor cortex; d) anxiety-like behavior and e) decreased survival (FIG. 4). In summary, these mice recapitulate molecular and severe, fatal neurodegenerative features of C9ORF72 ALS/FTD and provide an important tool to test the therapeutic efficacy of CRISPRi on C9 ALS/FTD.

Dosing and safety: Initial tests will be performed to assess dosing and safety of AAV-dCas9/gRNA to transduce the CNS of wildtype (FVB) mice via retro-orbital intravenous injections. The viral capsids, PHP.A and PHP.B, will be used to efficiently transduce the central nervous system, including neurons, glia, and oligodendrocytes of the brain and spinal cord. A small cohort of mice (n=4 mice per time point) will be injected with various doses of AAV dCas9/guide RNA, monitored for adverse reactions, and harvested at 2 or 4 weeks post-injection. Frozen and formalin-fixed paraffin embedded brains and spinal cords from these mice will be examined by immunohistochemistry (IHC), immunofluorescence (IF) and histopathology for expression of dCas9 and/or any associated CNS damage. Off-target effects on gene expression and RNA splicing will be monitored by RNAseq and will serve as a baseline for analysis in the C9-500 mice. The dosage of dCas9/guide RNA that gives the best CNS penetration and persistence with the least off-target effects will be selected for analysis in C9-500 BAC mice.

Timing of treatment: Disease onset in C9-500 mice is detectable at ~4 months of age, via DigiGait analyses of hindlimb gait abnormalities, prior to overt phenotypes, such as paralysis, weight loss and death. At ~5 months the mice develop overt disease phenotypes, including a slow progressive or an acute rapid-onset phenotype. By one year, 82% of mice from this line are phenotypic: 46% with overt cage-behavior abnormalities and 36% have died. The severity and lethality of the disease in these mice, coupled with the ability to detect onset prior to a rapid decline in health, provides an opportunity to test whether CRISPRi can prevent disease progression in a cohort of animals with early features of disease. A cohort of C9-500 BAC mice (n=20 per treatment group) will be treated at the beginning of disease onset (~4 months) with AAV dCas9 and HRE-targeting gRNA, or control gRNA. A small cohort (5 mice) will be sacrificed at 6 months, and others aged until 10 months. Brain, spinal cord and other tissues will be harvested from animals and either stored fixed or frozen for analyses. During the course of the experiment, animals will be monitored weekly for signs of disease progression (weight loss, limb paralysis, cage behavior) and tested at 4, 6, 8, and 10 months by DigiGait and open field analyses. C9-500 mice spend significantly shorter time in central region of the test chamber. Based on experience with the C9-500 mice, it is expected that roughly 40% of the untreated animals will develop an acute rapidly progressing phenotype over the course of the experiment and that will enable detection of a change in survival of 10% using 20 animals per treatment group. Tissues will also be harvested from mice that reach end-point due to disease during the length of the experiment. All mice will be assigned to treatment groups in a random manner, and scored and treated in double-blinded fashion.

Measuring molecular changes: RAN proteins expressed in these mice accumulate as aggregates in the brain. These aggregates are more abundant in end-stage and older symptomatic mice than in presymptomatic mice. RAN protein accumulation will be quantitated by IHC, IF and ELISA in the brain and spinal cord to determine whether CRISPRi alters the spatial and temporal distribution of RAN protein accumulation. Analysis of RAN protein accumulation following both short (~2 months of treatment/6 month mice) and long (~6 months of treatment/10 month mice) treatment will determine whether RAN accumulation is halted and/or reversed by CRISPRi. In parallel, frozen brain and spinal cord sections (5-10 µm) will be examined for sense and antisense foci, as well as RNA levels by qRT-PCR, at each time point. Impacts on the transcriptome will also be measured using RNAseq. Results will be compared to existing RNAseq data from patient tissues.

Figure 13:
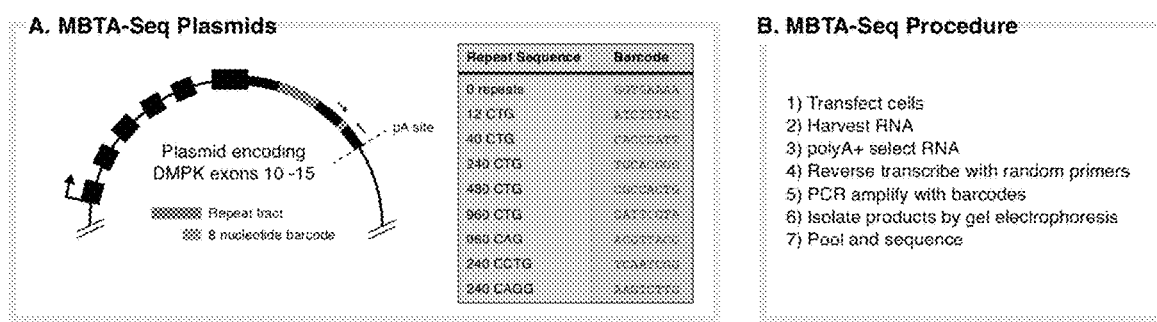
FIGS. 13A-B are diagrams showing Measurement of Barcoded Transcripts by Amplicon Sequencing (MBTA-Seq). Related to FIG. 7. A) is a schematic illustrating barcoded plasmids containing various repeats of different lengths followed by unique 8-nt barcodes. The table lists the unique barcodes for each repeat type. B) is a diagram of the MBTA-Seq protocol followed to measure levels of transcripts expressed from barcoded plasmids.

Measuring neurodegeneration: Neurodegeneration will be monitored at both 6 and 10 months. Neuromuscular junction abnormalities and neuronal loss in multiple brain and spinal cord regions will be monitored by IHC/IF. Because cortical layers II/III and V undergo dramatic neurodegeneration in untreated animals, this area will be used to assess whether CRISPRi reduces neurodegeneration. Differences in the distribution and appearance of RAN-positive cells relative to signs of neurodegeneration will be assayed by IHC/IF double-labeling methods and stereological techniques. Penetration of the dCas9/guide RNA will also be confirmed via IF, IHC and ELISA. Disease progression will be monitored by weight loss, DigiGait, and open field analyses. The efficacy of CRISPRi to prevent acute disease progression and increase survival will be evaluated. For all experiments, the mice will be evaluated in a blinded manner as to genotype and treatment group. Small molecules identified that impede HRE transcription can be analyzed in similar in vivo studies.

dCas9-gRNA complexes reduce abundance of repeat-containing RNAs in a length-, PAM-, and strand-dependent manner. dCas9 impedes transcription of expanded microsatellite repeats more potently than non-repetitive sequences because expanded repeats may: 1) present challenges for RNA Pol II elongation even under normal conditions; and 2) allow for high levels of dCas9 recruitment using a single guide RNA (gRNA) sequence, forming a substantial block to the elongating polymerase (FIG. 7A). A plasmid-based strategy was employed in cell culture to examine the effects of dCas9 recruitment on transcription of CTG/CAG repeats that occur in DM1, FECD, HD, and SCAs. Plasmids containing 0, 12, 40, 240, 480, or 960 CTG repeats located >1.5 kilobases downstream of the TSS in the DMPK 3' UTR were utilized. To recruit dCas9 to these repeats, gRNAs targeting CTG/CAG repeats in each of 3 possible nucleotide phases of the non-template strand, and 1 phase of the template strand were designed (FIG. 7B, left panel). Each PAM was, therefore, constrained to CAG, AGC, GCA, or CTG. An amplicon-based deep sequencing assay called "Measurement of Barcoded Transcripts by Amplicon Sequencing" (MBTA-Seq) was developed to precisely measure the expression of the repeat transcripts (FIG. 13). For this assay, plasmids were modified by introducing distinct 8 nucleotide barcodes downstream of each CTG repeat tract. RNA was harvested from cells transfected with these plasmids, polyA+ selected, amplified by RT-PCR across the barcode region but avoiding the repeat containing region, and deep sequenced (FIG. 13). This assay was highly reproducible and allowed quantitation of multiple repeat-containing transcripts in the same pool of cells. In the presence of dCas9 and $(CAG)_6$ (SEQ ID NO: 1) gRNA, a dramatic reduction in expression of RNAs containing expanded CUG repeats was observed (FIG. 7B, right panel). Knockdown efficiency increased with the number of repeats, presumably due to the increased number of dCas9-gRNA complexes recruited. Twelve CTG repeats, likely recruiting at most a single dCas9-gRNA complex, showed ~50% repeat-containing RNA remaining, and 40 CTG repeats showed ~25% remaining. Repeat lengths >240 CTG showed only ~5% remaining. $(AGC)_6$ (SEQ ID NO:4) and $(GCA)_6$ (SEQ ID NO:5) gRNAs showed poor knockdown efficiency, consistent with previously described SpCas9 PAM preferences, where NGG is best, NAG is second best, and NCG/NTG are equally disfavored. $(CUG)_6$ (SEQ ID NO:3) gRNA showed little to no knockdown of transcripts containing expanded CUG repeats, potentially due to a weak PAM as well as targeting to the template strand. Importantly, dCas9 was required for decreased expression of repeat-containing transcripts, as presence of gRNAs alone did not lead to knockdown (FIG. 14A).

These observations suggest that recruitment of dCas9-gRNA complexes can impede transcription of expanded microsatellite repeat tracts in a repeat length-dependent manner. However, these experiments were performed using transiently transfected plasmids, which may not accurately model all aspects of transcriptional regulation in a genomic context. Furthermore, experiments to assess binding of protein complexes to DNA loci are most commonly performed using genomic targets and not plasmids. Therefore, a HeLa cell line was established in which transgenes for each of the 6 CTG repeat lengths, with associated barcodes, were stably integrated (FIG. 14B). To measure DNA binding by dCas9-gRNA complexes, chromatin immunoprecipitation (ChIP) was performed against dCas9 in the presence of $(CAG)_6$ gRNA or non-targeting control gRNA. Similar to MBTA-Seq, the barcodes were deep sequenced to quantitate abundance of immunoprecipitated DNA encoding each repeat length. To confirm transcriptional repression in this cell line, RNA abundance was measured by MBTA-Seq following transfection of dCas9-gRNA complexes. It was observed that dCas9-gRNA binding to DNA increased as a function of repeat length, concomitant with a decrease in relative RNA abundance, when comparing $(CAG)_6$ (SEQ ID NO: 1) gRNA to control (FIG. 7C). In a genomic context, dCas9-gRNA reduced the abundance of transcripts containing 960 CUG repeats (SEQ ID) NO: 24) to ~20%, and was associated with ~8-fold increased binding relative to genomic loci without CTG repeat tracts. These observations suggest that binding of dCas9-gRNA complexes to DNA impedes transcription of repeat tracts, and that both binding and potency of transcriptional inhibition increases with the number of repeats.

To test whether dCas9-gRNA complexes can impede transcription of other expanded repeats, CCTG repeat tracts, which cause DM2 were assayed, and similar reduction in expression of CCUG repeat-containing RNAs was observed (FIG. 7D). Here, the tetranucleotide repeat allowed testing of 4 distinct gRNAs targeting the non-template strand, $(CAGG)_5$ (SEQ ID NO:6), $(AGGC)_5$ (SEQ ID NO:7), $(GGCA)_5$ (SEQ ID NO:8), and $(GCAG)_5$ (SEQ ID NO:9), corresponding to AGG, GGC, GCA, and CAG PAMs, respectively. Consistent with PAM preferences of SpCas9, knockdown was most efficient with the $(CAGG)_5$ gRNA, although the $(AGGC)_5$ (SEQ ID NO:7) and $(GCAG)_5$ (SEQ ID NO:9) gRNAs were also quite effective, in contrast to the $(CCUG)_5$ (SEQ ID NO:15) gRNA. Similar to studies of expanded CUG repeats, presence of gRNAs alone did not lead to knockdown (FIG. 14C).

To study how the PAM and targeted strand separately influence the efficacy of transcriptional blockade, and to clarify DNA versus RNA-targeting mechanisms, $(CAG)_{960}$ (SEQ ID NO: 21) and $(CAGG)_{240}$ (SEQ ID NO:22) plasmids suitable for MBTA-Seq were generated. These constructs are identical to their $(CTG)_{960}$ (SEQ ID NO:23) and $(CCTG)_{240}$ (SEQ ID NO:14) repeat-containing counterparts except for the repeat tract and barcode. MBTA-Seq was then used to measure the efficiency of $CUG_{960}$ (SEQ ID NO:24) or $CAG_{960}$ (SEQ ID NO:21) knockdown in the presence of either $(CAG)_6$ (SEQ ID NO:21) or $(CUG)_6$ (SEQ ID NO:24) gRNA (FIG. 7E). By testing all four combinations, PAM-dependent effects were separated from strand-dependent effects. Targeting the non-template DNA strand reduced expression more effectively than targeting the template strand. Specifically, $(CUG)_{960}$ (SEQ ID NO:24) was reduced to ~5% by a $(CAG)_6$ (SEQ ID NO:1) gRNA, while $(CAG)_{960}$ (SEQ ID NO:21) was reduced to ~40% by the same gRNA. These two conditions effectively compare targeting of non-template vs. template strand, controlling for the CAG PAM. Similarly, (CAG)$_{960}$ (SEQ ID NO:21) was reduced to ~50% by the (CUG)$_6$ (SEQ ID NO:3) gRNA, and (CUG)$_{960}$ (SEQ ID NO:24) remained relatively high at ~97%. Again, targeting of the non-template strand was more efficient than targeting of the template strand, controlling for the CTG PAM.

PAM-dependent effects were quantified by comparing abundance of (CTG)$_{960}$ (SEQ ID NO: 23) in the presence of (CAG)$_6$ (SEQ ID NO:1) gRNA relative to abundance of (CAG)$_{960}$ (SEQ ID NO: 21) in the presence of (CUG)$_6$ gRNA. Here, both gRNAs target the non-template strand, but use different PAMs. ~5% RNA remained with the CAG PAM, and ~55% RNA remained with the CTG PAM, controlling for targeted strand, consistent with the CAG PAM being more effective. Similarly, measurement of (CAG)$_{960}$ (SEQ ID NO:21) RNA in the presence of (CAG)$_6$ gRNA and (CTG)$_{960}$ (SEQ ID NO:23) RNA in the presence of (CUG)$_6$ (SEQ ID NO:3) gRNA allows comparison of both PAMs, controlling for targeted strand. Again, more effective silencing was observed with a CAG PAM (~40% RNA remaining) as compared to the CTG PAM (no change in RNA). Similar trends were observed with CCTG/CAGG repeats (FIG. 7F). (CCUG)$_{240}$ was reduced to ~5% by (CAGG)$_5$ (SEQ ID NO:6) gRNA and (CAGG)$_{240}$ (SEQ ID NO:22) to ~55% by (CAGG)$_5$ (SEQ ID NO:6) gRNA (non-template vs. template strand, AGG PAM). Although the same template vs. non-template effect was not observed when silencing with a CTG PAM, the (CCTG)$_5$ (SEQ ID NO:25) gRNA was largely ineffective, showing little to no silencing.

Figure 8:
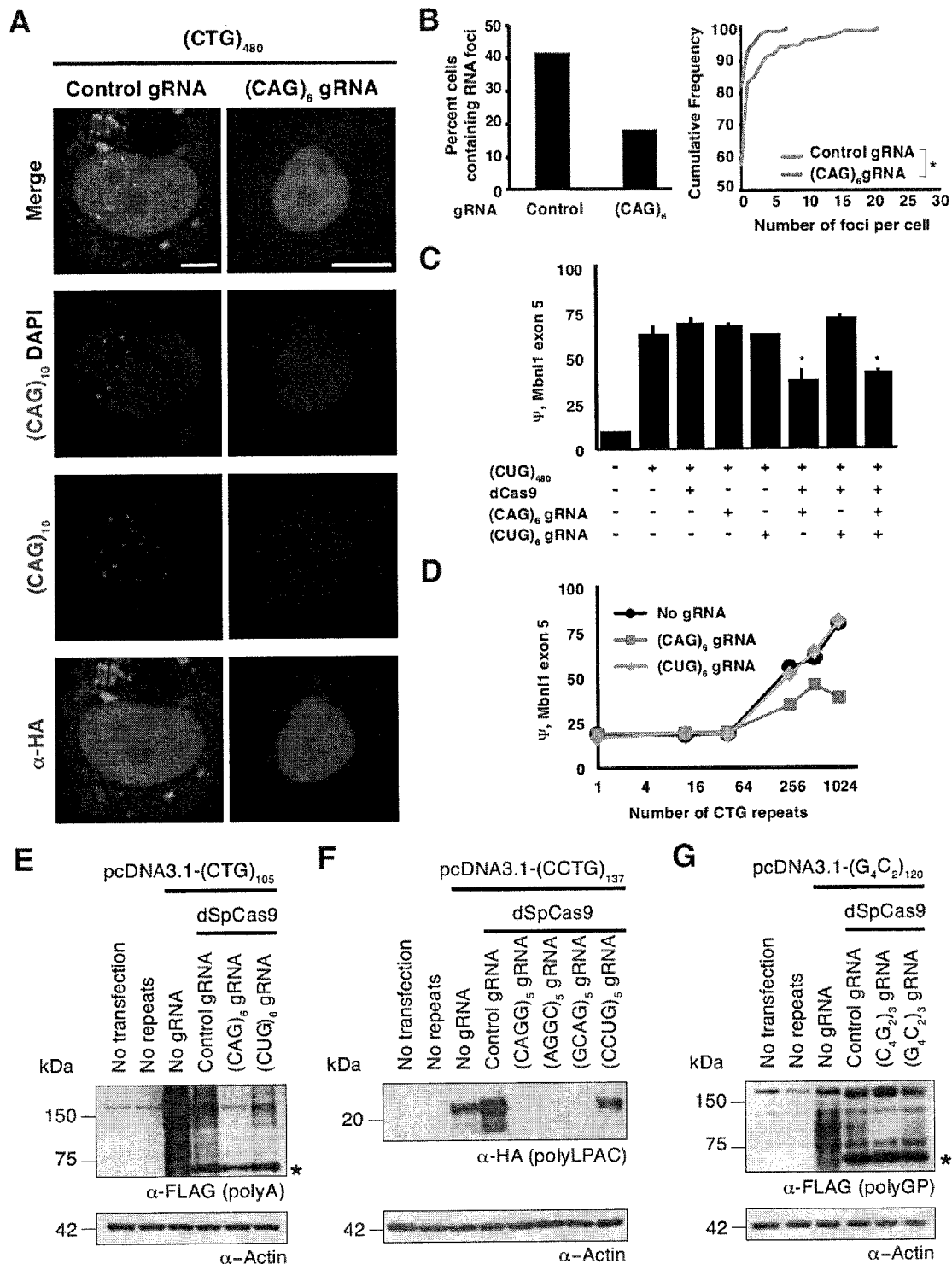
FIGS. 8A-G are photographs and graphs showing that transcriptional inhibition rescues molecular and cellular phenotypes in cell culture models of DM1, DM2, and C9ORF72/ALS/FTD. A) is a series of photographs showing representative FISH-IF images of HeLa cells transfected with plasmids expressing $(CTG)_{480}$ repeats, HA-dCas9 and control or $(CAG)_6$ (SEQ ID NO:1) gRNAs. RNA foci are shown in red, dCas9 in green and DNA (DAPI) in blue. Scale bar: 10 µm B) is a bar graph (left panel) and a line graph (right panel) showing the quantitation of HA-positive cells showing nuclear RNA foci (left panel) and the cumulative density function of HA-positive cells with a given number of RNA foci (right panel), in the presence of dCas9 and control or $(CAG)_6$ gRNAs (Control: 139 cells, $(CAG)_6$: 111 cells, Kolmogorov-Smirnov test, *p<0.005). C) is a bar graph of $\Psi$ of MBNL1 exon 5 expressed in a minigene context in HeLa cells, in the presence of combinations of plasmids encoding $(CTG)_{480}$ repeats, dCas9, and $(CAG)_6$ (SEQ ID NO:1) or $(CUG)_6$ (SEQ ID NO:3) gRNAs. N>3 for all conditions (two-tailed T-test, *p<0.005) D) is a graph of $\Psi$ of the MBNL1 exon 5 minigene in HeLas, in the presence of plasmids encoding 0, 12, 40, 240, 480, or 960 CTG repeats, as well as dCas9 and $(CAG)_6$ (SEQ ID NO:1) or $(CUG)_6$ (SEQ ID NO: 3) gRNAs. N>3 for all conditions. Error bars are too small to be visible. E) is a photograph of a Western blot to detect FLAG-tagged poly-Ala RAN peptides expressed from DM1 CTG repeats. Cells were transfected with various combinations of plasmids encoding no or $(CTG)_{105}$ repeats with combinations of dCas9 and control, $(CAG)_6$ (SEQ ID NO:1) or $(CUG)_6$ (SEQ ID NO: 3) gRNAs. The peptides migrate as a 75 and 150 kD smear. The asterisk indicates a cross-reacting protein produced by the dSpCas9 plasmid. F) is a photograph of a Western blot against the HA-tagged LPAC RAN protein expressed from DM2 CCTG repeats. Cells were transfected with various combinations of plasmids encoding no or $(CCTG)_{137}$ (SEQ ID NO:18) repeats with combinations of dCas9 and control, $(CAGG)_5$ (SEQ ID NO:6), $(AGGC)_5$ (SEQ ID NO:7), $(GCAG)_5$ (SEQ ID NO:9) or $(CCUG)_5$ (SEQ ID NO:15), gRNAs. The peptide migrates at 20 kD. G) is a photograph of a Western blot against the FLAG-tagged poly-GlyPro RAN protein expressed from ALS $G_4C_2$ repeats. Cells were transfected with various combinations of plasmids encoding no or $(G_4C_2)_{120}$ (SEQ ID NO:20) repeats with combinations of dCas9 and control, $(C_4G_2)_3$ (SEQ ID NO: 10) or $(G_4C_2)_3$ (SEQ ID NO:11) gRNAs. The peptides migrate as a 75 and 120 kD smear. The asterisk indicates a cross-reacting protein produced by the dSpCas9 plasmid, β-Actin serves as the loading control and N=3 for E, F and G (representative blot shown).

Overall, these results separate the effects of PAM sequence and targeted strand in the context of transcriptional blockade. Furthermore, they support a model in which dGas9/gRNA complexes target repeat-containing DNA, because reductions in RNA abundance are achieved even when using gRNAs that are not complementary to transcribed RNAs.

dCas9-mediated transcriptional inhibition rescues splicing defects and blocks RAN translation in cell-based models of DM and C9ALS/FTD. Downstream symptoms of many repeat expansion diseases are caused by the expression of toxic RNA species, which sequesters RNA binding proteins necessary for cellular functions, causing downstream changes to the transcriptome and proteome. To assess whether dGas9-mediated transcriptional silencing can rescue molecular and cellular phenotypes in disease models, a HeLa cell-based model of DM1 was used, in which (CUG)$_{480}$ (SEQ ID NO:26) repeats are expressed from a plasmid. Co-expression of dCas9 and (CAG)$_6$ (SEQ ID NO:1) gRNA led to a reduction in the percentage of cells showing CUG-containing RNA foci, as well as a reduction in the number of foci per cell (FIG. 8A, B). Rescue of MBNL-dependent splicing misregulation, characteristic of DM1 cells was measured, using a splicing minigene reporter containing MBNL1 exon 5. The percent spliced in (psi, Ψ) of this exon is regulated by MBNL proteins, and changes from 10% in healthy HeLa cells to ~70% in cells expressing (CUG)$_{480}$ repeats. Co-transfection of dCas9 and (CAG)$_6$ (SEQ ID NO: 1) gRNA partially rescued splicing dysregulation, reducing Ψ to ~35% (FIG. 8C). This rescue required both dCas9 and (CAG)$_6$ (SEQ ID NO:1) gRNA, indicating that (CAG)$_6$ (SEQ ID NO:1) gRNA expression alone cannot neutralize toxic CUG RNA by displacing MBNL protein or facilitating degradation. Splicing defects in DM1 depend on total CUG repeat load; Ψ values for MBNL1 exon 5 increased with the length of the CTG repeat tract transfected into cells (FIG. 8D). Interestingly, co-expression of dCas9 and (CAG)$_6$ (SEQ ID NO:1) gRNA yielded a similar rescue of splicing across all repeat lengths exhibiting mis-splicing, i.e. 240, 480, and 960 CUG repeats.

Figure 9:
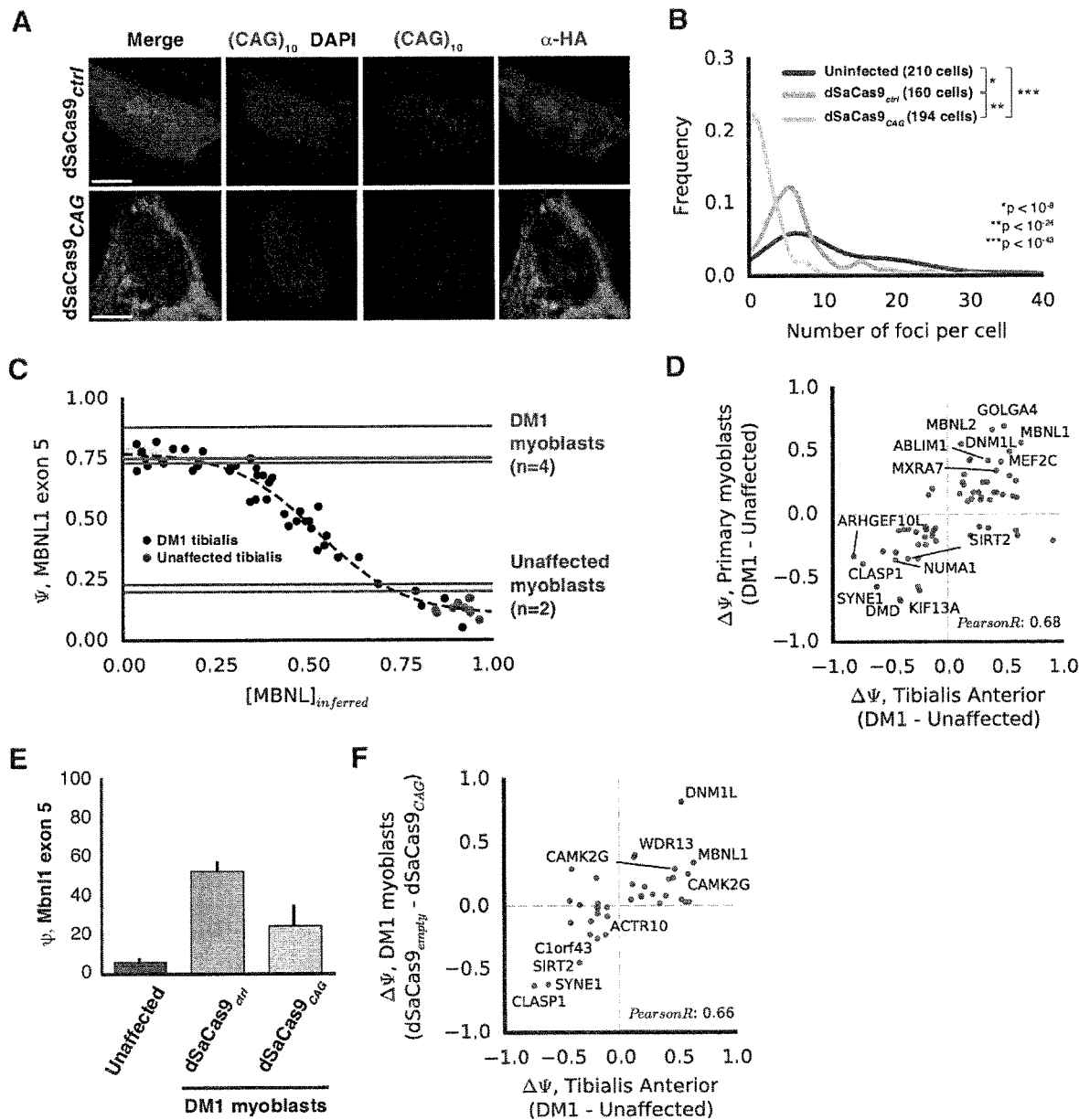
FIGS. 9A-F are photographs and graphs showing that AAV-dSaCas9 rescues molecular and cellular phenotypes in human DM1 myoblasts. A) is a series of photographs of representative FISH-IF images of DM1 myoblasts infected with AAV-dSaCas9-control or $(CAG)_6$ (SEQ ID NO: 1) gRNAs. RNA foci are shown in red, dCas9 in green, and DAPI in blue. Scale bar: 10 µm B) is a graph showing the probability density function of cells with a given number of RNA foci, in the presence of control or $(CAG)_6$ gRNAs (Kolmogorov-Smirnov test for statistical significance). C) is a graph of MISO estimates of MBNL1 exon 5 $\Psi$ in 11 unaffected and 44 DM1 TA biopsies plotted in order of $[MBNL]_{inferred}$ as previously described. A sigmoid curve was fit to these points and shown (dashed line) with 90% confidence intervals (gray shading). MISO estimates of MBNL1 exon 5 $\Psi$ values in unaffected and DM1 primary myoblast lines (2 and 4 replicates, respectively) are shown in blue and red lines, respectively, with ranges also shaded. D) is a scatter plot for splicing events regulated in both TA biopsies and the human myoblast lines described in (C). 115 splicing events were selected from TA biopsies based on best sigmoid fits with $[MBNL]_{inferred}$ as in (C). The x-axis of the scatter plot is the mean $\Psi$ in the most severely affected biopsies (<0.33 $[MBNL]_{inferred}$) minus the mean $\Psi$ across unaffected individuals. The y-axis of the scatter plot is the mean $\Psi$ in the DM1 myoblast minus the mean $\Psi$ in the unaffected myoblast line. Labeled points have $\Delta\Psi$>0.3 in both conditions, a sigmoid fit <1.3, and a y-axis monotonicity score >1 (see Examples). Pearson correlation is listed. E) is a bar graph of MBNL1 exon 5 $\Psi$, assessed by RT-PCR in unaffected myoblasts and DM1 myoblasts infected with AAV-dSaCas9-control or $(CAG)_6$ (SEQ ID NO:1) gRNAs. F) is a scatter plot illustrating changes in $\Psi$ in response to AAV-dSaCas9 $(CAG)_6$ (SEQ ID NO:1) gRNA, for splicing events exhibiting concordant behavior in (D). The x-axis is as in (D), but the y-axis is ΔΨ in DM1 myoblasts, AAV-dSaCas9-control gRNA treatment minus AAV-dSaCas9-(CAG)$_6$ (SEQ ID NO:1) gRNA treatment. Labeled points have ΔΨ>0.1 in both conditions and a y-axis Bayes Factor >5 (see Examples). Pearson correlation is listed.
Figure 15:
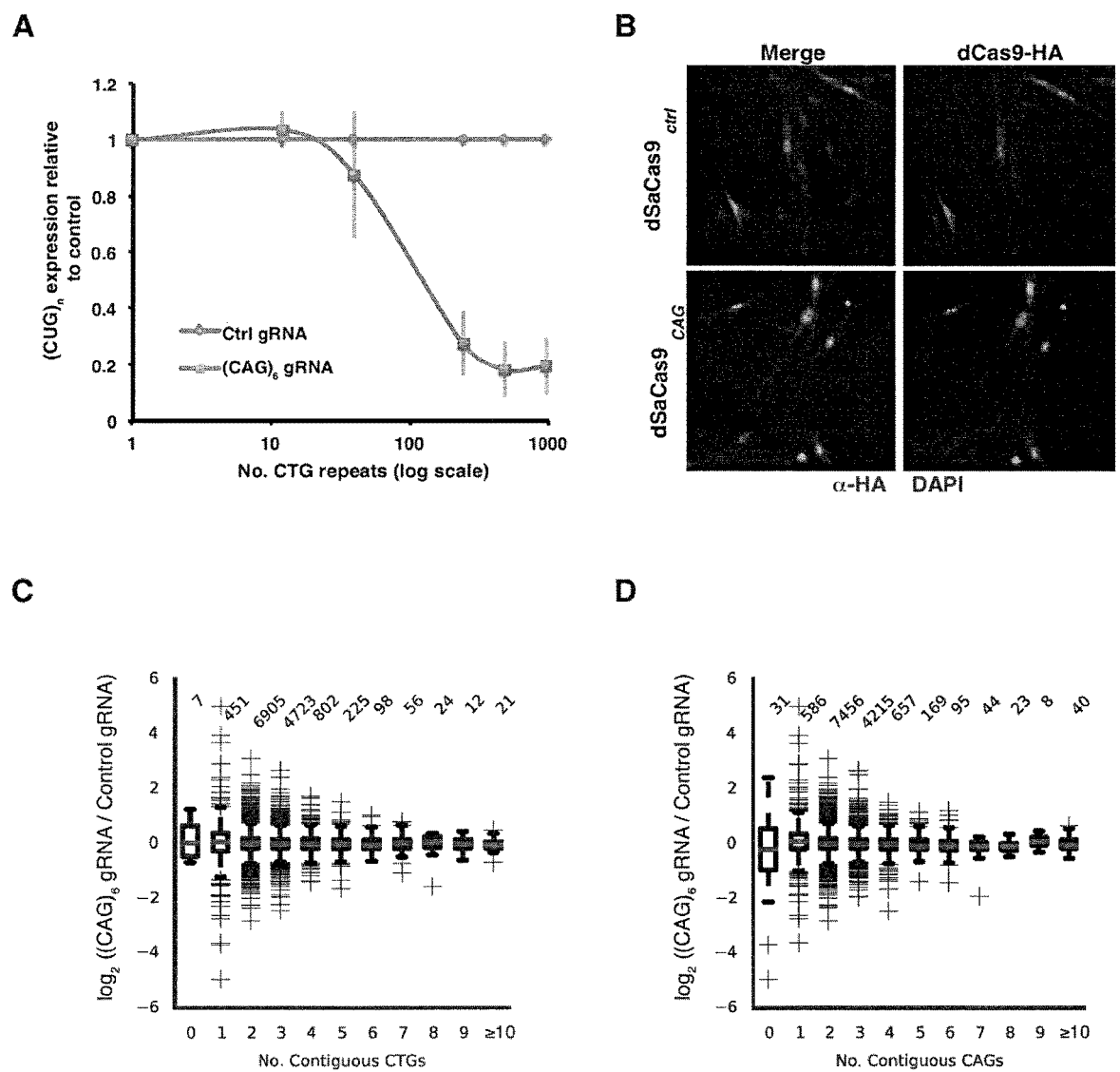
FIGS. 15A-D are graphs and photographs showing that transcriptional block of microsatellite repeat constructs by dSaCas9 in Hela cells and dSaCas9 localization in infected DM1 primary myoblasts. Related to FIG. 9. A) is a graph showing abundance of CUG repeat-containing RNA in the presence of control or (CAG)$_6$ (SEQ ID NO: 1) gRNA targeting 0-960 CTG repeat tracts relative to abundance of RNA with no CUG repeats in Hela cells B) is a series of photographs of immunofluorescence analyses to detect expression of dSaCas9 in DM1 primary myoblasts infected with AAV-dSaCas9$_{ctrl}$ (top) and AAV-dSaCas9$_{CAG}$ (bottom).

The CTG, CCTG, and G$_4$C$_2$ repeats associated with DM1, DM2, and C9ALS/FTD, respectively, undergo repeat-associated non-ATG (RAN) translation. dCas9-mediated transcriptional repression could also yield reduced RAN protein abundance. Western blot analyses of RAN peptides, facilitated by downstream protein tags, revealed reduction in CTG, CCTG, and G$_4$C$_2$ RAN product (FIG. 8E). In all three western analyses, RAN proteins were observed only in with repeat-containing plasmids, and were slightly reduced upon expression of a control, non-targeting gRNA, potentially due to competition of plasmids for transcriptional machinery. Consistent with measurements of CUG-containing RNA levels (FIG. 7B), the FLAG-tagged poly-Ala peptide translated from CUG repeats was dramatically reduced in the presence of (CAG)$_6$ (SEQ ID NO:1) gRNA, and modestly reduced in the presence of (CUG)$_6$ (SEQ ID NO:3) gRNA (FIG. 8E). Importantly, RAN protein was not reduced in the presence of (CAG)$_6$ gRNA alone without dCas9 (FIG. 14D). HA-tagged poly-LPAC translated from CCUG repeats was dramatically reduced in the presence of (CAGG)$_5$ (SEQ ID NO:6), (AGGC)$_5$ (SEQ ID NO:7), and (GCAG)$_5$ (SEQ ID NO:9) gRNAs (FIG. 8F), but not in the presence of (CCUG)$_5$ (SEQ ID NO:15) gRNA (FIG. 14E). To test effects of dCas9 on levels of poly-GlyPro translated from G$_4$C$_2$ repeats, two gRNAs were designed with NGG PAMs: (C$_4$G$_2$)$_3$ (SEQ ID) NO: 10) that would target the non-template strand and (G$_4$C$_2$)$_3$ (SEQ ID NO: 11) that would target the template strand. Consistent with studies of CTG and CCTG repeats, dCas9-gRNA complexes targeted to (G$_4$C$_2$)$_{120}$ (SEQ ID NO:20) exhibited silencing of RAN peptide in a strand-dependent manner (FIG. 8G), and did not occur in the presence of gRNA alone (FIG. 14F). While reduction in RAN protein was achieved with both gRNAs, silencing was more effective with gRNA targeting the non-template strand.

dCas9-mediated transcriptional inhibition reduces nuclear RNA foci and rescues splicing defects in human DM1 myoblasts. Whether this approach could impede transcription of expanded repeats in the native DMPK locus was tested in primary human DM1 myoblasts by delivering dCas9 via AAV. Due to AAV genome size limits, the smaller S. aureus Cas9 (SaCas9) was packaged with a U6 promoter-driven gRNA and deactivated via D10A and H557A mutations. Since dSaCas9 exhibits PAM preferences distinct from dSpCas9 (NNGRR versus NGG), MBTA-Seq was used to confirm that dSaCas9 with a (CAG)$_6$ (SEQ ID NO:1) gRNA could impede transcription of expanded CTG repeats in a length-dependent manner (FIG. 15A). Next, dSaCas9 was packaged with control or (CAG)$_6$ (SEQ ID NO:1) gRNA into AAV2/6, because the AAV6 capsid efficiently infects myoblasts in culture (FIG. 15B). dSaCas9 protein carrying 5 nuclear localization signals was found to be nuclear, although at times also cytoplasmic (FIG. 15B, FIG. 9A). Similar to studies in HeLa, the number of CUG repeat foci per cell was decreased in the presence of dSaCas9 and (CAG)$_6$ (SEQ ID NO:1) gRNA relative to control gRNA (FIG. 9A, B).

Although splicing events in DM1 patient muscle have been well characterized, cultured myoblasts do not express many transcripts present in mature muscle. The DM1 myoblasts described above as well as an unaffected line were further characterized to identify molecular changes appropriately modeling in vivo DM1 biology. Four RNAseq libraries were created from the DM1 cells and 2 from the unaffected line, each grown in low or high serum conditions. To identify splicing changes appropriately modeling those observed in human DM1 muscle, a high confidence set of DM1-relevant splicing events was defined by re-analyzing a set of 55 transcriptomes (44 DM1 and 11 unaffected) from human tibialis biopsies (GSE86356). Splicing events were identified whose inclusion level, Ψ, strongly correlated to the concentration of free, functional MBNL protein in the affected tissue. Sigmoid curves were fit describing the relationship between MBNL concentration and Ψ, for example for MBNL1 exon 5 (FIG. 9C). The best-fitting events were selected (see Examples), and their dysregulation (ΔΨ, Tibialis anterior, DM1 minus unaffected) was plotted against dysregulation observed in the DM1 myoblasts (ΔΨ, Primary myoblast, DM1 minus unaffected) (FIG. 9D). These filtering steps yielded a set of myoblast splicing events that models splicing events in human DM1 muscle.

To assess splicing rescue by dCas9, RT-PCR was performed to measure the inclusion level of MBNL1 exon 5. While viral infection with an AAV encoding dSaCas9 and control gRNA yielded a Ψ of ~50%, infection with AAV encoding dSaCas9 and $(CAG)_6$ (SEQ ID NO: 1) gRNA rescued Ψ to ~20% (FIG. 9E). Splicing transcriptome-wide by RNAseq was assessed, and analysis was performed on those exons in the myoblasts whose changes are concordant with changes observed in tibialis biopsies (lower left and upper right quadrants, FIG. 9D), and whose baseline Ψ values are less than 0.33 units apart when comparing tibialis to myoblasts. Several exons were successfully rescued, and a correlation of ~0.66 was observed between dysregulation in tibialis (ΔΨ, DM1 minus unaffected) versus rescue by dSaCas9 and $(CAG)_6$ gRNA (ΔΨ, control gRNA minus $(CAG)_6$ (SEQ ID NO:1) gRNA) (FIG. 9F). To assess potential off-target changes in gene expression for other transcripts with genomic CTG or CAG repeat tracts, unaffected myoblasts were treated with AAV-dSaCas9 and $(CAG)_6$ (SEQ ID NO:1) gRNA or control gRNA and RNA-Seq was performed. The longest contiguous CTG or CAG repeat tracts in all pre-mRNAs in the human genome were enumerated, and none were found to exceed 24 repeats; maximums were 24 CTG in TCF4 and 22 in AR. No differences in gene expression were observed that depended on the length of repeat tracts, for both CTG or CAG repeats (FIG. 15C, D). These observations suggest that dSaCas9 targeted to CTG repeat tracts can impede transcription of expanded CUG repeats, relieve MBNL sequestration, and restore splicing homeostasis in human cells containing DM1 repeat expansions, with selectivity that depends on the extreme repeat lengths commonly found in symptomatic tissue.

dCas9-mediated transcriptional inhibition reduces RNA foci, rescues Clcn1 expression, and decreases myotonia in a mouse model of DM1. It was assessed whether dCas9 could impede transcription of expanded CTG repeats in a well-established mouse model of DM1, $HSA^{LR}$. These mice carry a human skeletal actin transgene containing 250 CTG repeats in the 3' UTR and exhibit molecular, cellular, and phenotypic properties characteristic of DM patients. To assess efficacy of this approach independent of potential in vivo drug delivery challenges, extensor digitorum longus muscle (EDL) fibers were dissected and cultured ex vivo. As CTG repeat expression in this model is driven by the HSA promoter, RNA foci are ubiquitous and numerous in myonuclei, showing FISH signal in ~80% of myonuclei (FIG. 10A, Top panel). This remained at similar levels following 2 days of AAV treatment with dSaCas9 and control gRNA, but fell to ~50% with dSaCas9 and $(CAG)_6$ (SEQ ID NO:1) gRNA. (FIG. 10B). FISH signal intensity, quantitated in >1400 nuclei per condition (see Examples, FIG. 16), was dramatically decreased in fibers treated with dSaCas9-$(CAG)_6$ gRNA relative to control gRNA and untreated fibers (FIG. 10C). These observations suggest that effective delivery of dSaCas9-$(CAG)_6$ to muscle fibers ex vivo is sufficient to significantly reduce RNA foci load within 2 days.

Given previous reports of immune reactivity against Cas9, especially following intramuscular injection, AAV-dSaCas9-gRNA was administered by temporal vein injection at postnatal day 2, prior to full establishment of immune tolerance. AAV2/6 or AAV2/9 carrying dSaCas9 and $(CAG)_6$ (SEQ ID NO:1) or control gRNA was injected. Five weeks following injection, electromyography was performed to analyze myotonia in tibialis anterior and gastrocnemius muscles (FIG. 11A). Wild type FVB mice showed no myotonia, an Mbnl1 KO mouse showed myotonia in 100% of needle insertions, and $HSA^{LR}$ mice showed myotonia in 87-100% of insertions. $HSA^{LR}$ injected with AAV6-dSaCas9-control gRNA showed myotonia levels similar to uninjected $HSA^{LR}$ (87%). However, $HSA^{LR}$ mice injected with AAV6-dSaCas9-$(CAG)_6$ gRNA showed a reduction in myotonia, with some showing myotonia in only 33-50% of insertions. Interestingly, nearly all mice injected with AAV2/6 showed rescue while only 1 mouse injected with AAV9 showed rescue (FIG. 16D).

Splicing patterns of Clcn1 mRNA in treated mice were measured because mis-splicing of chloride channel 1 (Clcn1) is well-established to mediate myotonia in DM1 and in $HSA^{LR}$ mice. Surprisingly, when analyzing RNA extracted from bulk muscle tissue, significant rescue in Clcn1 splicing, or other MBNL-dependent splicing events could not be detected. Because myotonia is measured by assaying individual bundles of fibers, it is possible that some regions of muscle may be rescued and not others, and that any potential change in isoform composition in these regions may be diluted in analyses of bulk tissue. This is consistent with a roughly ~2.5-fold increase in myonuclei per fiber over the first 4 weeks of post-natal development, which could also dilute the proportion of myonuclei containing AAV episomes. AAV6-delivered dSaCas9 distribution in EDL fibers revealed mosaic expression, with rare fibers showing region-specific nuclear signal for dCas9 (FIG. 11B), and most fibers showing absence of dCas9. Control immunofluorescence experiments against lamin A showed ubiquitous and consistent labeling of all myonuclei, ruling out potential staining artifacts (FIG. 16E). In spite of mosaic dSaCas9 distribution, 5-15% of fibers showed complete loss of CUG RNA foci (FIG. 11C). Furthermore, extent of reduction in RNA foci correlated to strength of myotonia rescue across animals. Reduction of RNA foci in some nuclei raised the possibility that proper Clcn1 splicing could be achieved in a subset of nuclei, and that these mRNAs may spread locally throughout the fiber to produce functional Clcn1 protein. Indeed, mice treated with $(CAG)_6$ (SEQ ID NO:1) gRNA showed increased Clcn1 staining at muscle membranes relative to mice treated with control gRNA (FIG. 11D), but Clcn1 protein was localized only to a subset of fibers per muscle section. These observations are consistent with observations of myotonia elimination in a subset of fibers, yet absence of splicing rescue when assessing bulk tissue. In summary, dCas9 can, in principle, rescue disease phenotypes via transcriptional repression, but widespread rescue of molecular events in muscle will require efficient delivery to a large proportion of myonuclei expressing toxic RNA.

The teachings disclosed herein 1) form the basis for a therapeutic to treat diseases characterized by expanded microsatellite repeats, including ALS, as well as 2) provide important information necessary to benchmark and interpret molecular and physiological effects of this and other related therapeutic strategies. Small molecules that are capable of blocking expanded microsatellite repeat transcription, including HRE transcription, and a gene therapy approach to blocking expanded microsatellite repeat transcription, including HRE transcription, and accurately measuring the effects of blocking expanded microsatellite repeat transcription, including blocking HRE transcription in the context of C9ORF72/ALS/FTD are contemplated.

Example 1

Figure 5:
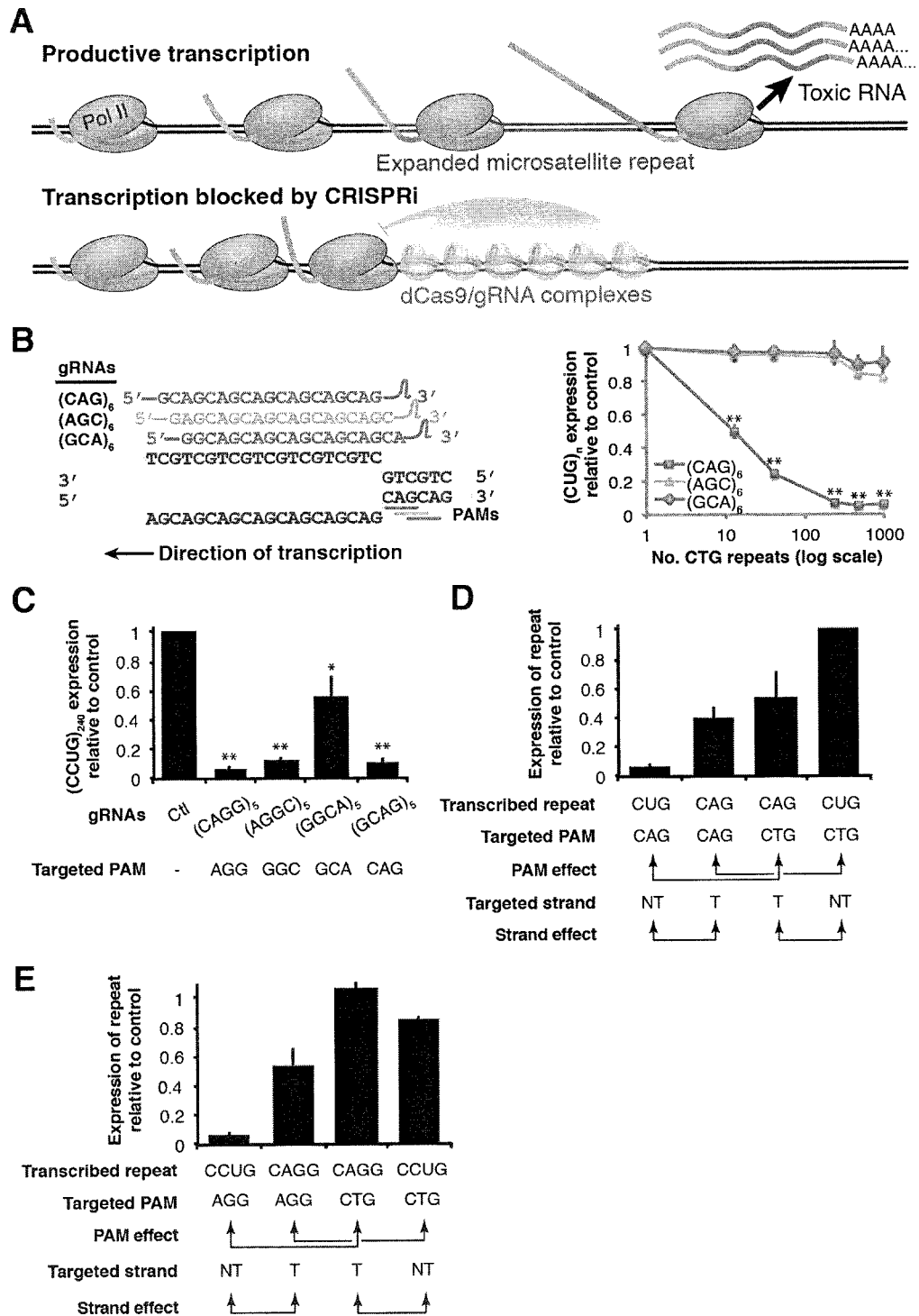
FIGS. 5A-E are diagrams and graphs showing that deactivated Cas9 impedes transcription of expanded microsatellite repeats in length, PAM, and strand-dependent manner. A) shows a proposed model for how recruitment of multiple dCas9/gRNA complexes to expanded microsatellite repeats impedes transcription of mRNA. B) is a schematic of proposed gRNA hybridization to microsatellite repeat tract (shown are SEQ ID NOs: 30-33). Abundance of CUG repeat-containing RNA in the presence of dCas9/gRNAs $(CAG)_6$ (SEQ ID NO:1), $(AGC)_6$ (SEQ ID NO:4), or (GCA) (SEQ ID NO:5) targeting the repeat tract, relative to RNA containing 0 repeats in the presence of control gRNA. C) is a bar graph showing the abundance of CCUG repeat-containing RNA in the presence of dCas9/gRNAs $(CAGG)_5$ (SEQ ID NO:6), $(AGGC)_5$ (SEQ ID NO:7), $(GGCA)_5$ (SEQ ID NO:8), $(GCAG)_5$ (SEQ ID NO:9), relative to RNA with 0 repeats in the presence of control gRNA. D) is a bar graph showing the abundance of RNAs containing 960 CUG repeats (SEQ ID NO:24) or 960 CAG repeats (SEQ ID NO:21) in the presence of $(CAG)_6$ (SEQ ID NO:1) gRNA or $(CTG)_6$ (SEQ ID NO:2) gRNA. Comparisons are drawn between PAM sequence, as well as targeted strand (non-template, NT vs. template, T). E) is a bar graph showing the abundance of RNAs containing 240 CCUG repeats (SEQ ID NO: 19) or 240 CAGG repeats (SEQ ID NO:22), in the presence of $(CAGG)_6$ (SEQ ID NO:12) gRNA or $(CCTG)_6$ (SEQ ID NO:13) gRNA, as in (D). Error bars are plotted as the mean+SD values of 4 experiments.

Catalytically deactivated Cas9 (dCas9) inhibits transcription of CTG and CCTG repeat-containing transcripts (CRISPRi). Deactivated Cas9 can inhibit transcription, but typically relies on steric blocking in bacteria or requires a KRAB domain to inhibit initiation in mammalian cells when targeted to promoters. Inhibition of elongating RNA Pol II in mammalian gene bodies showed ~40% reduction at best. However, long repeats could recruit multiple dCas9 proteins using a single guide RNA (gRNA) sequence, resulting in enhanced steric blockade, consistent with the "CRISPRi collision model", leading to paused RNAP and disassembly (FIG. 5A). To test this hypothesis, expression of mRNAs containing multiple CUG repeat lengths in the presence of control, CAG-targeting, or CTG-targeting gRNAs was measured. Three CTG-targeting gRNAs were tested, where the register of repeats relative to the PAM (CAG, AGC, and GCA) was shifted (FIG. 5B). A CAG-targeting gRNA was also tested. Consistent with *S. pyogenes* PAM preferences, the gRNA targeting CAG repeats matching a CAG PAM was highly effective, leading to a repeat length-dependent reduction in expression relative to an mRNA with 0 repeats (FIG. 5B). Similar reduction was observed with expression of 240 CCTG repeats (SEQ ID NO:14) when using guide RNAs targeting $(CAGG)_5$ (SEQ ID NO: 5), $(AGGC)_5$ (SEQ ID NO:7), $(GCAG)_5$ (SEQ ID NO:9), but not $(GGCA)_5$ (SEQ ID NO:8), again consistent with PAM preferences (FIG. 5C). To measure the dependency of transcriptional blockade efficiency on PAM sequence versus targeted strand, expression of plasmids expressing 960 CAG repeats was compared to those expressing 960 CTG repeats (SEQ ID NO:21), in the presence of $(CAG)_6$ (SEQ ID NO:1) gRNA or $(CTG)_6$ (SEQ ID NO:2) gRNA. It was observed that targeting the non-template strand using a CAG PAM was most efficient (FIG. 5D). Similar trends were observed with CCTG/CAGG repeats (FIG. 5E). Similar transcriptional blockade of expanded microsatellite repeats using a deactivated version of *S. aureus* Cas9 was also observed.

Figure 6:
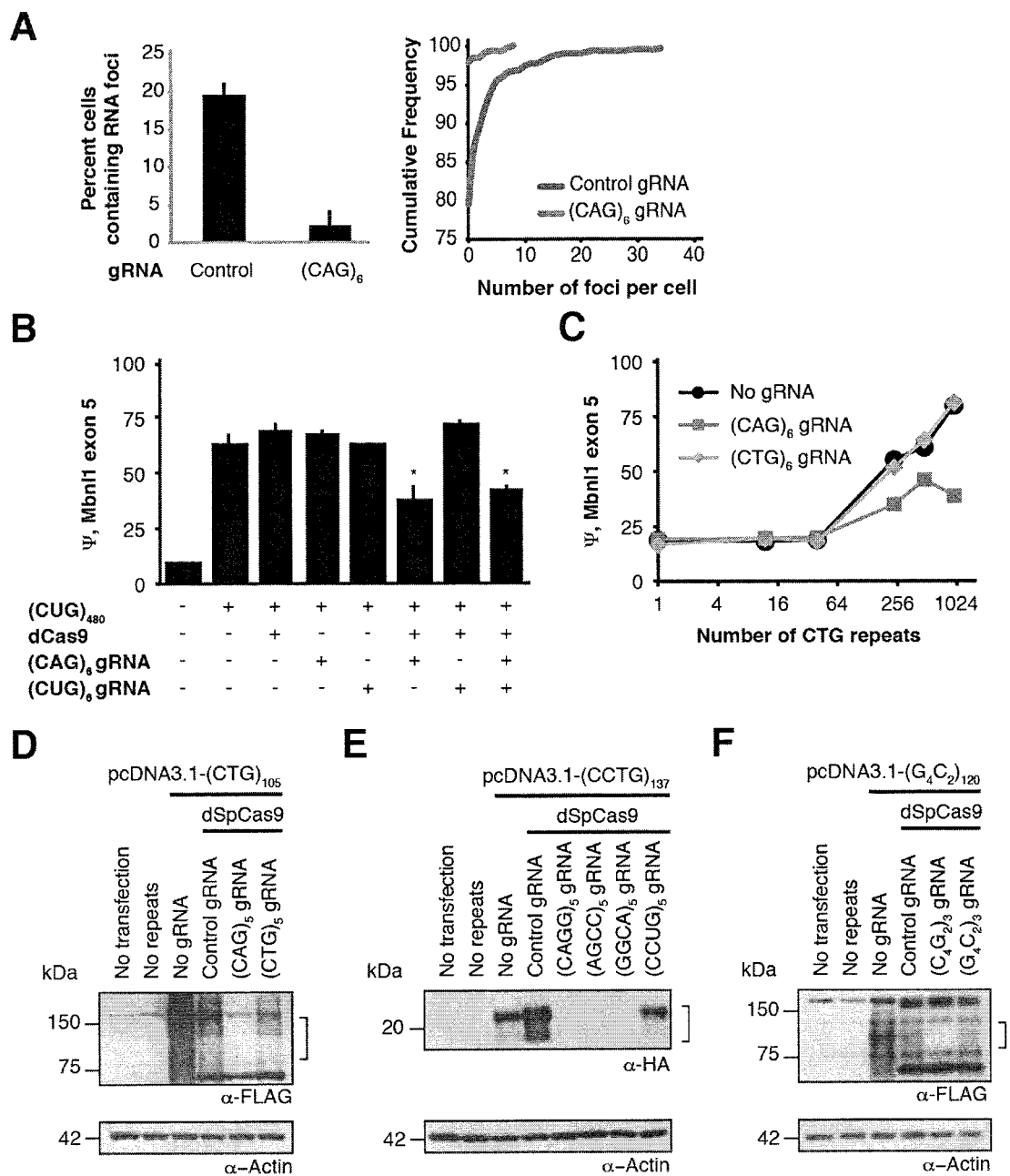
FIGS. 6A-F are graphs and photographs showing transcriptional inhibition by CRISPRi rescues molecular and cellular phenotypes in cell culture models of DM and other microsatellite expansion repeats. A) is a bar graph showing the percentage of cells containing RNA foci in the presence of dCas9 and control or $(CAG)_6$ (SEQ ID NO:1) gRNA (left panel), and a graph showing the cumulative distribution of number of foci per cell in HeLa cells transfected with 480 CUG repeats (SEQ ID NO:26) (right panel). B) is a bar graph showing the inclusion level of MBNL1 exon 5 transcribed from a minigene reporter, in the presence and absence of 480 CUG repeats, dCas9, and gRNAs that target the template or non-template strand of the repeat-containing plasmid. C) is a graph showing the inclusion level of MBNL1 exon 5 in the presence and absence of $(CAG)_6$ gRNA (SEQ ID NO:1), $(CTG)_6$ (SEQ ID NO:2) gRNA, or no gRNA. D)-F) are photographs of Western blots showing that dCas9 and repeat-targeting gRNAs suppress RAN translation of CTG (D), CCTG (E), and $G_4C_2$ (F) repeats, as assayed using protein tags in frame with RAN peptides. RAN products are indicated using brackets. Shown are $(CAG)_5$ (SEQ ID NO:34), $(CTG)_5$ (SEQ ID NO:37), $(CAGG)_5$ (SEQ ID NO:6), $(AGGC)_5$ (SEQ ID NO: 7), $(GGCA)_5$ (SEQ ID NO:8), $(CCUG)_5$ (SEQ ID NO:15), $(C_4G_2)_3$ (SEQ ID NO:10), and $(G_4C_2)_3$ (SEQ ID NO:11).

To assess downstream functional consequences of transcriptional blockade in the context of disease models, CUG repeat RNA foci formation was measured in HeLa cells transfected with plasmids encoding CTG repeats, in the presence of dCas9 and $(CAG)_6$ (SEQ ID NO:1) or control gRNA. Targeting dCas9 to repeats led to a reduction in the percentage of cells with RNA foci, as well as the number of foci per cell (FIG. 6A). CUG repeats are known to sequester members of the Muscleblind-like (MBNL) RNA binding proteins, which regulate alternative splicing; by assaying a splicing minigene encoding MBNL1 exon 5, splicing rescue was observed in the presence of dCas9 and $(CAG)_6$ (SEQ ID NO:1) gRNA (FIG. 6B). Pathogenic splicing was dependent on repeat length, but rescue could be achieved even in the presence of 960 repeats (FIG. 6C). Finally, non-ATG dependent repeat-associated translation, which occurs in the context of expanded microsatellite repeats, was suppressed in the presence of dCas9 and gRNAs targeting appropriate repeat tracts. CTG RAN product, CCTG RAN product, and GGGGCC RAN product were all suppressed by CRISPRi, as assayed by Western blotting of peptide tags downstream of each repeat tract (FIG. 6D-F).

Example 2: Experimental Model and Subject Details

Cell Lines

Human cell lines and primary cells were utilized in this study. Patient myoblast cell lines were derived from muscle biopsies under a University of Florida-approved IRB protocol with informed consent from all patients. Information on the genders of the patient cells is unavailable. All cells were grown under standard conditions of 37° C. and 5% $CO_2$ in media supplemented with 10% fetal bovine serum.

Animals

In vivo animal studies were performed on $HSA^{LR}$ transgenic mice in this study. Both males and females were used in EMG analysis, which was performed at 5 weeks of age, as by this time point mice display appreciable myotonia. All these studies were performed in accordance with guidelines and regulations of the Institutional Animal Care and Use Committee (IACUC) at the University of Florida.

Method Details

Cell Culture, Cell Lines and Transfection

HeLa and HEK293T cells were cultured in 1×DMEM supplemented with 10% fetal bovine serum and 1% Penicillin/Streptomycin at 37° C. and 5% $CO_2$. The DM1 primary myoblast cells were obtained by G. Xia. The clinical data of research subjects from who muscle biopsies were obtained, have been described before (Xia et al., 2013). Muscle biopsies were performed using 7G UCH Muscle Biopsy Needle (#8066, Cadence Science). Samples were cut into small pieces and seeded into a 6 cm dish. Myoblasts were expanded at a 1:2 ratio in myoblast growth media (Skeletal Muscle Cell Growth Medium-2, Lonza, #CC 3245) at 37° C. and 5% $CO_2$. For viral transductions, these primary myoblasts were maintained in the growth medium for 3 days and then switched to Differentiation media (DMEM-F12 supplemented with 2% horse serum) for 3 days.

Plasmid DNA transfections of HeLa and HEK293T cells were performed using Trans-IT LT1 (MirusBio) as per manufacturer's instructions. For RNA and FISH analyses, HeLa cells were harvested or processed 72 hours post transfection.

Cloning Barcoded Repeats and gRNA Plasmids

Non-barcoded plasmids carrying 0, 12, 40, 240, 480, 960 CTG repeats ($CTG_n$) and 960 CAG repeats ($CAG_{960}$, SEQ ID NO:21) were obtained from Tom Cooper (Baylor College of Medicine). Plasmids with 0 and 12 repeats were modified so that their vector backbones were identical to the others, and carried the ampicillin resistance gene. The $(CCTG)_{240}$ plasmid was created as in Philips et al (Philips et al., 1998). In brief, oligonucleotide fragments 5'-TCGA $(CCTG)_{20}$C-3' (SEQ ID NO: 27) and 5'-TCGAG $(CAG)_{20}$-3' (SEQ ID NO:28), were phosphorylated, annealed, gel isolated, and concatemerized by T4 DNA ligase. Concatemers not in a head to tail orientation were digested by SalI and XhoI. Concatemers were gel-isolated and cloned into the SalI site of $CTG_0$. To create $CAGG_{240}$ (SEQ ID NO:2), $CTG_{960}$ (SEQ ID) NO: 23) was digested with SalI and HindIII and a new fragment was introduced which included HindIII and AgeI restriction sites (DT_MCS). $CCTG_{240}$ was digested with XmaI and HindIII and ligated with DT_MCS digested with HindIII and AgeI to reverse orientation of the repeats and form $CAGG_{240}$ (SEQ ID NO:22).

For MBTA-Seq, each repeat-containing plasmid was barcoded by introducing a fragment containing a random 8-nt sequence at the PflMI restriction site located downstream of the repeats via In-Fusion cloning (Clontech). Clones were sequenced to confirm that each repeat containing plasmid carried a unique barcode (FIG. 13A). Barcoded $CTG_{960}$ and $CAG_{960}$ plasmids were generated by digesting $(CTG)_{960}$ (SEQ ID NO:23) and $(CAG)_{960}$ (SEQ ID NO:21) with HindIII and AccIII and ligating gBlocks containing unique barcodes with the digested plasmids.

The dCas9 gRNAs were cloned into an AflII-digested U6 expression vector by annealing oligos as previously described (Mali et al., 2013). The dSaCas9 gRNAs were cloned into BsaI-digested vector by annealing oligos as previously described (Ran et al., 2015).

Generating Barcoded Repeat Expressing HeLas

To generate stable cell lines, the DMPK expression cassette was removed from each of the 6 barcoded plasmids and inserted into pAC156 (obtained from Albert Cheng), a plasmid with Piggybac transposon terminal repeats as well as a puromycin selection cassette. All 6 plasmids were transiently transfected together with the Piggybac mPB transposase into HeLa, and selected by puromycin. Single cells were isolated by flow cytometry, and colonies were cultured in 96 well plates. 48 colonies were expanded and subjected to MBTA-Seq to screen for integration and expression of all 6 plasmids.

dCas9 Chromatin and RNA IP dCas9 ChIP and RIP experiments were performed on the HeLa cell line containing the six different repeat lengths (CTG0-960) integrated into genome. 10 cm plates of ~80% confluent cells were transfected with the pXdCas9 and U6 expression vectors expressing the dCas9 protein and the control or $(CAG)_6$ (SEQ ID NO: 1) gRNAs respectively, using the manufacturers guidelines. For ChIP, 48 hours after transfection cells were crosslinked with 1% formaldehyde for 20 minutes at room temperature. Cross-linking reactions were stopped by addition of glycine to a final concentration of 0.125 M. Cells were then harvested, washed with phosphate buffered saline and pelleted. 1 mL of Lysis Buffer 1 (50 mM Hepes [pH 7.5], 140 mM NaCl, 1 mM EDTA, 10% glycerol, 0.5% Igepal, 0.25% Triton X-100) was added to the cells and rocked at 4° C. for 10 minutes. After spinning, the cells were incubated in Lysis Buffer 2 (10 mM Tris-HCl [pH 8.0], 200 mM NaCl, 1 mM EDTA, 0.5 mM EGTA) for 10 minutes at RT. Nuclei were pelleted and resuspended in 1 mL of Lysis Buffer 3 (10 mM Tris-HCl [pH 8.0], 100 mM NaCl, 1 mM EDTA, 0.5 mM EGTA, 0.1% Na-deoxycholate and 0.5% N-lauroylsarcosine) and subjected to sonication in a Covaris S220 to obtain DNA fragments averaging 4 kb in length. One-twentieth of the total chromatin served as input. The remaining material was used in the IP, which was performed using the HA-tag (C29F4) rabbit mAb conjugated to magnetic beads (Cell Signaling Technologies) at 4° C. overnight to pull down the HA-tagged dSpCas9 and interacting DNA. Beads were washed 7 times with wash buffer (50 mM Hepes [pH 7.6], 500 mM LiCl, 1 mM EDTA, 1% Igepal and 0.7% Na-Deoxycholate). Immunocomplexes were eluted from the beads with elution buffer (50 mM Tris-HCl, 10 mM EDTA and 1% SDS) at 65° C. for 15 minutes. Crosslinks in the IP and input were reversed overnight at 65° C. and treated with RNase A and proteinase K to remove RNAs and proteins. DNA was extracted with phenol-chloroform and precipitated with ethanol. The barcoded region associated with each repeat length was amplified from the isolated DNA fragments using primers containing adapters facilitating deep-sequencing.

For the RNA IP experiments, 48 hours after transfection, cells were harvested in 1 mL of lysis buffer (100 mM Kcl, 5 mM MgCl2, 10 mM HEPES [pH 7.0], 0.5% Igepal, 1 mM DTT, 100 U/mL SUPERase In RNase inhibitor (Thermo Fisher), 2 mM vanadyl ribonucleoside complexes solution, 25 uL/mL protease inhibitor cocktail). One-twentieth of the resulting lysate was used as input and the remaining lysate was incubated with HA-tag (C29F4) rabbit mAb conjugated to magnetic beads (Cell Signaling Technologies) at 4° C. overnight to pull down the HA-tagged dSpCas9 and interacting RNA. Beads were washed with the lysis buffer four times at 4° C. and immunocomplexes were eluted off with 0.1% SDS and proteins removed using proteinase K at 50° C. for 30 minutes. RNA was isolated using the Direct-zol RNA miniprep kit (Zymo Research) and contaminating DNA was eliminated using TURBO DNase (Thermo Fisher). cDNA was generated using Superscript IV Reverse Transcriptase (Thermo Fisher) and subsequently barcoded regions were amplified using flanking primers carrying sequences suitable for deep sequencing.

FISH and Immunofluorescence (IF) Analyses

To detect nuclear RNA foci, cells or muscle fibers were fixed with 4% PFA for 10 minutes at room temperature followed by ice cold RNAse free 70% ethanol for 30 mins. Fixed samples were washed with a 25% formamide wash buffer at 30° C. for 30 mins and then hybridized with a CalFluor 610 conjugated $(CAG)_{10}$ oligonucleotide (Biosearch Technologies) in a 25% formamide hybridization buffer overnight at 300° C. Finally samples were washed two times at 30° C. with wash buffer for 30 minutes to an hour, incubated with DAPI (1 mg/mL) and mounted in Vectashield. Further IF analysis was performed on HeLa cells and DM1 myoblasts to detect the presence of the dCas9-HA protein. After excess oligonucleotide was washed off, the cells were blocked in 3% normal goat serum in 1% Triton X-100-PBS for 30 mins at room temperature, incubated with anti-HA antibody (1:500, #3724, Cell Signaling Technologies) overnight at 4° C., washed with 1×PBS, incubated with Alexa Fluor 488 conjugated anti-rabbit secondary antibody (1:500, Life Technologies) for 2 hours, washed and incubated with DAPI for 5 mins and mounted in Vectashield. Slides were imaged using the Zeiss LSM 880 Confocal Laser Scanning Microscope. IF analysis to detect dCas9 in mouse muscle fibers from the EDL of mice injected with AAV6-dSaCas9-(CAG)6 (SEQ ID NO:1) was conducted as described above, except samples were fixed with 100% isopropanol at −20° C. for 10 mins.

Clcn1 was detected in mouse muscle by performing IF on frozen muscle sections of the TA. Frozen muscle was sectioned into 10 uM slices, fixed with 100% acetone at −20° C. for 20 minutes, washed with 0.3% Triton X-100-PBS and incubated with rabbit anti Clcn1 (1:100, #CLC11-S, Alpha Diagnostic International) overnight at 4° C. Samples were incubated with goat anti-rabbit Alexa Fluor 568 (1:500, Thermo Fisher) for 2 hours at RT and then treated with DAPI and mounted in Vectashield.

Western Analyses for RAN Peptides

HEK293Tcells were transfected with one of the following plasmids that express tagged RAN translated products: pcDNA-6×Stop-$(CTG)_{150}$-3×(FLAG-HA-cMyc-His), pcDNA-6×Stop-$(CCTG)_{137}$-3×(FLAG-HA-cMyc-His) or pcDNA-6×Stop-$(G_4C_2)_{120}$-3×(FLAG-HA-cMyc-His). These cells were co-transfected with the pXdCas9 plasmid expressing the dCas9 protein, and U6 expression vectors expressing the control gRNA or gRNA's targeting either strand of the CTG, CCTG and $G_4C_2$ repeats ((CAG)$_6$ (SEQ ID NO:1) or (CUG)$_6$ (SEQ ID NO:3) gRNAs, (CAGG)$_5$ (SEQ ID NO:6), (AGGC)$_5$ (SEQ ID NO:7), (GCAG)$_5$ (SEQ ID NO:9), or (CCUG)$_5$ (SEQ ID NO: 15) gRNAs and $(C_4G_2)_3$ (SEQ ID NO:10) or $(G_4C_2)_3$ (SEQ ID NO:11) gRNAs, respectively).

72 hours after transfection, cells in each well of a 12-well tissue culture plate were gently rinsed 1× with PBS and lysed in 200 ul of RIPA Buffer (50 mM Tris-Cl pH 7.4, 150 mM NaCl, 0.1% Na-Deoxycholate, 1% NP-40, 0.5% SDS) with protease inhibitors for 30 minutes on ice. Genomic DNA was sheared by 8-10 passages through a 21-gauge needle. The resulting lysate was centrifuged at 18,000×g for 15 min and the supernatant was collected. The protein concentration of the lysate was determined using Pierce™ BCA Protein Assay. Equal amounts of protein were loaded and separated on a 4-12% NuPage Bis-Tris gel (Novex) and transferred to a nitrocellulose membrane (Amersham). The membrane was blocked in 5% milk in PBS-Tween20 (0.05%) for 1 hour and probed with anti-FLAG (1:2000) or anti-HA (1:1000) antibody in 1% milk solution in PBS-Tween20 (0.05%) overnight at 4° C. After the membrane was incubated with anti-mouse and anti-rabbit HRP (1:10,000) for 2 hours at room temperature, the bands were detected using the SuperSignal™ West Femto Maximum Sensitivity Substrate as per manufacturers protocol (Zu et al., 2011).

Recombinant AAV Production

Viral production was achieved through transfection of HEK293T cells cultured in 150 mm plates with the pAAV6 serotype packaging plasmid (Rutledge et al., 1998), pXX6 helper plasmid that contains the adenovirus E4, VA and E2a helper regions (Xiao et al., 1998) and AAV2-ITR containing plasmid expressing dSaCas9 and the control or (CAG)$_6$ (SEQ ID NO:1) gRNA (generated from the SaCas9 plasmid pX601-AAV-CMV::NLS-SaCas9-NLS-3×HA-bGHpA; U6::BsaI-sgRNA, Addgene #61591). Transfections were carried out using the TransIT-LT1 transfection reagent and recommended protocols (MirusBio). Cells were harvested between 48 h and 72 h post-transfection, recombinant AAV2/6 virus was purified by iodixanol step gradients followed by vector concentration and buffer exchange with lactated Ringer's in an Apollo 150 kDa concentrator (Orbital Biosciences) (Zolotukhin et al., 2002). Virus titers were determined using the Quant-iT Picogreen dsDNA assay kit (Life Technologies) (Piedra et al., 2015) and found to be $\sim 10^{11}$ vg/mL.

Muscle Fiber Isolation

Single muscle fibers were isolated from 3-4 week old HSA$^{LR}$ mice as described previously (Pasut et al., 2013). Briefly, the EDL was dissected and digested with a 0.2% Collagenase Type I in DMEM solution in a 37° C. water bath for 1 hour without agitation. The digested muscle was then flushed with DMEM to separate out individual muscle fibers. Fibers were cultured in DMEM containing 20% FBS overnight before infection with AAV.

Transduction of Myoblasts and Muscle Fibers

Virus carrying dSaCas9 and control or (CAG)$_6$ gRNA was used to infect human DM1 primary myoblast cell lines and HSA$^{LR}$ mouse EDL muscle fibers. To determine whether blocking expression of the CTG repeats in the human myoblasts affected the presence of RNA foci and splicing of MBNL targets, cells were grown to 60% confluency on CC2 chamber slides and infected for 6 days (3 days in growth media plus 3 days in differentiation media) with viral titers of 109. To analyze the effects on RNA foci in HSA$^{LR}$ muscle fibers, 10-20 muscle fibers were cultured in wells of a 96 well plate and infected with a 109 viral titer for 48 h.

Quantitating Signal Intensity of Nuclear Foci

Figure 16:
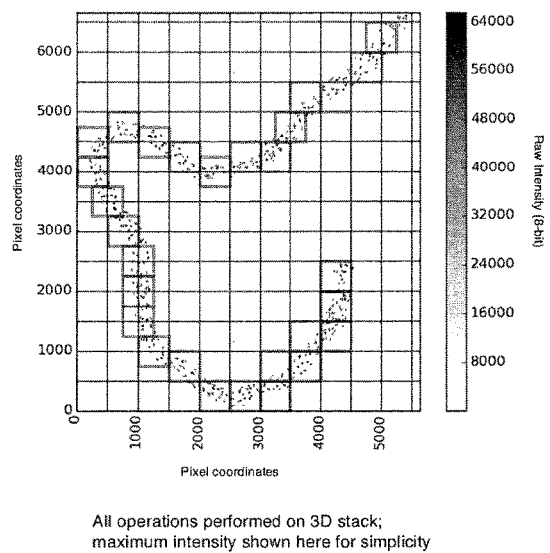
Figure 16:
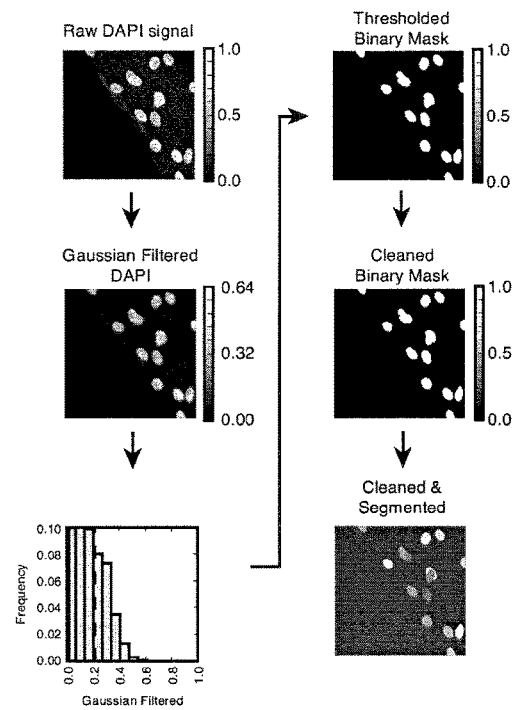
Figure 16:
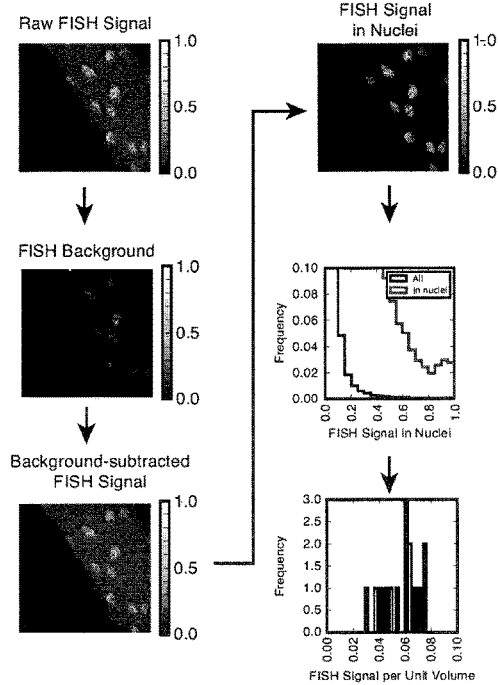
Figure 16:
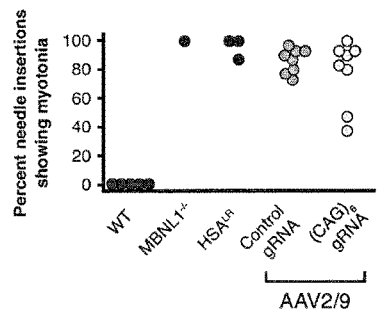
Figure 16:
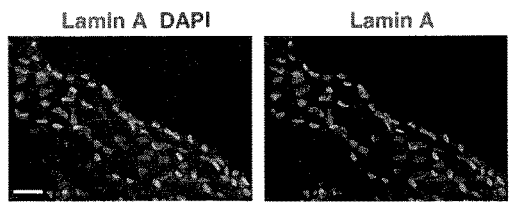

Python scripts were written to quantitate intensity of FISH signal from RNA foci within nuclei of muscle fibers (python functions are listed below, and also see FIG. 16). Regions of interest were defined across each tile-scanned z-stack image obtained by confocal imaging. To identify and segment nuclei, 16-bit intensity values were scaled to lie between 0 and 1 (skimage.img_as_float). Then, a gaussian filter of standard deviation 3 pixels was applied to the raw DAPI signal (skimage.filters.gaussian), and a threshold of mean+ 5*standard deviation of the gaussian filtered signal was used to generate a binary mask. Holes were filled (scipy.ndimage.fill_holes), and a binary opening operation was performed to remove salt noise (skimage.morphology.binary_opening with ball structured element of radius 2). Nuclei were segmented and labeled (skimage.measure.label), and objects with pixel volume <1000 or >20000 were removed. FISH signal was scaled to lie between 0 and 1 as above, and a grayscale opening operation was performed to measure background (skimage.morphology.opening with a ball structured element of radius 3). This background intensity multiplied by 3 was subtracted from the FISH signal to yield background-subtracted FISH signal. The binary nucleus mask was applied to this signal, and total intensity was measured within each nucleus, and divided by the nuclear volume in pixels, to obtain the final FISH signal per unit volume for each nucleus. This procedure was applied to all regions of interest across all fibers.

Analysis of RNAseq Data 100 ng of RNA was used to prepare RNA-Seq libraries using the KAPA Ribo-Erase Strand-Specific kit. Samples were pooled and sequenced on the NextSeq 500 Version 2, using a High-Output 2×75 kit. Reads were mapped to hg19 by Hisat2, and splicing events were quantitated by MISO. Ψ values from DM tibialis biopsies were fit to sigmoid curves using 4-parameter estimation, where $\Psi = \Psi_{min} + (\Psi_{max} - \Psi_{min})/(1+e^{-slope*([MBNL]inferred-EC50)})$, using python/scipy packages. The [MBNL]$_{inferred}$ value was taken from Wagner et al (Wagner et al., 2016). The "fit error" was evaluated by taking the sum of squared errors between observed Ψ and Ψ as predicted by the sigmoid curves. Events consistently regulated between non-DM1 and DM1 myoblasts were identified using a modified monotonicity test (Wang et al., 2015), ΔΨ>0.1, BF >5) where the 2 non-DM1 libraries were grouped together, and 4 DM1 libraries were grouped together. For FIG. 11B, events with <1.3 sigmoid fit error and >1 monotonicity Z-score were selected for display. For FIG. 11F, only events identified in FIG. 11B to lie in the upper right or lower left quadrants were further analyzed; in addition, events were required to exhibit <0.33 difference in Ψ between cells treated with AAV-dSaCas9-control gRNA and non-DM1 tibialis biopsies. Raw RNA-Seq reads for these libraries are publicly available (GEO accession number pending).

Electromyography

To determine whether expression of dCas9-(CAG)$_6$ rescued myotonia in the HSA$^{LR}$ mice, mice were injected with AAV6-dSaCas9 and control or (CAG)$_6$ (SEQ ID NO:1) gRNA at 1010 viral genomes per mouse via the temporal vein at P2. Myotonia was assessed by electromyography (EMG) at 5 weeks of age as described previously (Kanadia et al., 2003). EMG was performed under general anaesthesia (intraperitoneal ketamine, 100 mg/kg; xylazine, 10 mg/kg) using 30 gauge concentric needle electrodes with at least 15 needle insertions per muscle in the hindlimb muscles, gastrocnemius and TA. Myotonic discharges were denoted as a percentage of the total number of insertions. In FIG. 11A, each point represents one of the hindlimb muscles from a single animal, but in some animals, both muscles were tested. N=2 mice for control gRNA and N=4 mice for $(CAG)_6$ (SEQ ID NO:1) gRNA.

Data and Software Availability

The accession number for the data reported herein is GEO: GSE103997, which is incorporated herein by reference.

The invention claimed is:

1. An adeno-associated virus (AAV) vector, an AAV virion or an AAV viral particle comprising:
   a viral capsid;
   a nucleic acid encoding a deactivated *S. aureus* Cas9 (dSaCas9) that is not fused to a transcriptional repressor; and
   a nucleic acid encoding a CTG repeat-targeting guide RNA (gRNA).

2. The AAV vector, AAV virion or AAV viral particle according to claim 1, wherein said guide RNA comprises the nucleic acid sequence $(CAG)_6$ (SEQ ID NO:1).

* * * * *